(12) United States Patent
Cloutier et al.

(10) Patent No.: US 11,471,299 B2
(45) Date of Patent: *Oct. 18, 2022

(54) INTERBODY CAGE DEVICE AND METHODS OF USE

(71) Applicant: NOVAPPROACH SPINE LLC, Alachua, FL (US)

(72) Inventors: Raymond Cloutier, Alachua, FL (US); Michael Macmillan, St. Petersburg, FL (US); Thomas Terramani, San Diego, CA (US); Elezar Tonev, Bradenton, FL (US)

(73) Assignee: NovAppoach Spine LLC, Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/502,171

(22) Filed: Oct. 15, 2021

(65) Prior Publication Data

US 2022/0031467 A1    Feb. 3, 2022

Related U.S. Application Data

(63) Continuation of application No. 17/444,084, filed on Jul. 30, 2021.

(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/446* (2013.01); *A61F 2/30749* (2013.01); *A61F 2/30771* (2013.01);

(Continued)

(58) Field of Classification Search
CPC .................................................... A61F 2/4455
See application file for complete search history.

(56) References Cited

U.S. PATENT DOCUMENTS

| | | |
|---|---|---|
| 8,328,870 B2 | 12/2012 | Patel et al. |
| 9,451,940 B2 | 9/2016 | Spann |

(Continued)

FOREIGN PATENT DOCUMENTS

WO    2017175024 A2    10/2017

OTHER PUBLICATIONS

Rajaraman et al., Division of Neurosurgery, New Jersey Medical School; "Visceral and vascular complications resulting from anterior lumbar interbody fusion"; J. Neurosurg: Spine / vol. 91 / Jul. 1999; pp. 1-5.

(Continued)

*Primary Examiner* — Andrew Yang
(74) *Attorney, Agent, or Firm* — FisherBroyles LLP

(57) ABSTRACT

A spinal interbody fusion device for use in a plurality of surgical approaches includes a cage, a top end, a bottom end, and at least a first side representing the width of the cage and at least a second side representing a length of the cage. The cage includes fixation holes and inserter holes, with each fixation hole being configured for accepting a screw or anchor and each inserter hole being accessible for one or more surgical approaches for performing a spinal fusion. Also included are methods for selecting a size of an intervertebral implant and methods of surgically approaching a spine of a patient for spinal surgical procedures.

20 Claims, 23 Drawing Sheets

Related U.S. Application Data

(60) Provisional application No. 63/059,160, filed on Jul. 30, 2020.

(52) U.S. Cl.
CPC .......... *A61F 2/4611* (2013.01); *A61F 2/4657* (2013.01); *A61F 2002/3085* (2013.01); *A61F 2002/30158* (2013.01); *A61F 2002/30537* (2013.01); *A61F 2002/30784* (2013.01); *A61F 2002/4658* (2013.01)

(56) References Cited

U.S. PATENT DOCUMENTS

| | | | |
|---|---|---|---|
| 9,895,235 | B2 | 2/2018 | Melkent et al. |
| 10,799,370 | B2 | 10/2020 | Bae et al. |
| 2010/0211106 | A1 | 8/2010 | Bowden et al. |
| 2017/0056199 | A1* | 3/2017 | Altarac ............... A61F 2/4637 |
| 2019/0083281 | A1 | 3/2019 | Zubok et al. |
| 2019/0231551 | A1 | 8/2019 | Freedman et al. |
| 2019/0262142 | A1* | 8/2019 | Bennett ............... A61F 2/4455 |
| 2020/0015981 | A1 | 1/2020 | Melkent et al. |

OTHER PUBLICATIONS

Bassani et al.; https://doi.org/10.1007/s00586-018-5659-0; "A new "keyhole" approach for multilevel anterior lumbar interbody fusion: the perinavel approach—technical note and literature review"; European Spine Journal 27:1956-1963 (2018); pp. 1-8.

Fantini et al.; ISSN 2218-5836 (online); "Access related complications during anterior exposure of the lumbar spine" World Journal of Orthopedics; (2013); pp. 1-5.

Sasso et al.; Lippincott Williams & Wilkins, Inc ; Spine vol. 30, No. 6, pp. 670-674; "Analysis of Operative Complications in a Series of 471 Anterior Lumbar Interbody Fusion Procedures"; (2005); pp. 1-5.

Bianchi et al.; Annals of Vascular Surgery; "Anterior Retroperitoneal Lumbosacral Spine Exposure: Operative Technique and Results"; International Journal of Vascular Surgery; (2003); pp. 1-6.

Kuang et al.; Hindawi Publishing Corporation; "Applying the Mini-Open Anterolateral Lumbar Interbody Fusion with Self-Anchored Stand-Alone Polyetheretherketone Cage in Lumbar Revision Surgery"; vol. 2016, Article ID 1758352, 9 pages http://dx.doi.org/10.1155/2016/1758352; (2016); pp. 1-10.

Mobbs et al.; Global Spine Journal; Original Article 147; ISSN 2192-5682; "Approach-Related Complications of Anterior Lumbar Interbody Fusion: Results of a Combined Spine and Vascular Surgical Team"; Global Spine J 2016;6:147-154.; (2016); pp. 1-8.

Klezl et al.; Asian Spine Journal; "Incidence of Vascular Complications Arising from Anterior Spinal Surgery in the Thoraco-Lumbar Spine"; Asian Spine J 2014; 8(1):59-63; http://dx.doi.org/10.4184/asj.2014.8.1.59; (2014); pp. 1-5.

Mobbs et al.; "Lumbar interbody fusion: techniques, indications and comparison of interbody fusion options including PLIF, TLIF, MI-TLIF, OLIF/ATP, LLIF and ALIF"; http://dx.doi.org/10.3978/j.issn.2414-469X.2015.10.05; (2015); pp. 1-17.

Mayer; "Microsurgical Anterior Lumbar Interbody Fusion 45 (Mini-ALIF): The Lateral Retroperitoneal Approach to L2/3, L3/4, and L4/5"; Chapter 45; (2006); pp. 1-14.

Xu et al.; Annals of Translational Medicine.; "Minimally invasive anterior, lateral, and oblique lumbar interbody fusion: a literature review"; Ann Transl Med 2018;6(6):104; (2018); pp. 1-12.

Oppenheimer et al.; Neurosurg Focus / vol. 27; "Minimally invasive spine technology and minimally invasive spine surgery: a historical review"; Neurosurg Focus 27 (3):E9, (2009); pp. 1-15.

Mamuti et al.; Wolters Kluwer Health, Inc.; "Mini-open Anterior Lumbar Interbody Fusion for Recurrent Lumbar Disc Herniation Following Posterior Instrumentation"; Spine vol. 41, No. 18, pp. E1104-E1114; (2016) pp. 1-11.

Hynes et al.; Medtronic Sofamor Danek USA, Inc.; OLIF25; "Oblique Lateral Interbody Fusion For L2 to L5 Surgical Fechnique"; (2012) pp. 1-32.

Saraph et al.; Springer-Verlag; Comparison of conventional versus minimally invasive extraperitoneal approach for anterior lumbar interbody fusion; Eur Spine J (2004) 13 :425-431; DOI 10.1007/s00586-004-0722-4; (2004); pp. 1-7.

Gumbs et al.; American Medical Association; "The Open Anterior Paramedian Retroperitoneal Approach for Spine Procedures"; RCH SURG/vol. 140; (2005); pp. 1-5.

Garg et al.; Western Vascular Society; Society for Vascular Surgery; Vascular complications of exposure for anterior lumbar interbody fusion; (2010); pp. 1-5.

Hamdan et al.; Society for Clinical Vascular Surgery; "Vascular injury during anterior exposure of the spine"; (2008); pp. 1-5.

Bassani et al.; Scientific Research Publishing; International Journal of Clinical Medicine; "Video-Assisted Anterior Retroperitoneal Approach to the Lumbar Spine. A Minimal Invasive Technique Improved by the Use of Endoscopic Camera to Treat Lumbar Spine Diseases"; http://www.scirp.org/journal/ijcm ; http://dx.doi.org/10.4236/ijcm.2016.71009 (2016); pp. 1-7.

International Searching Authority; "Notification of Transmittal of the International Search Report and the Written Opinion of the International Searching Authority, or the Declaration" dated Dec. 9, 2021; PCT Application No. PCT/US2021/071063; pp. 1-10 (Year: 2021).

* cited by examiner

Supine ATP Approach

AL-LIF Approach

ALIF Approach

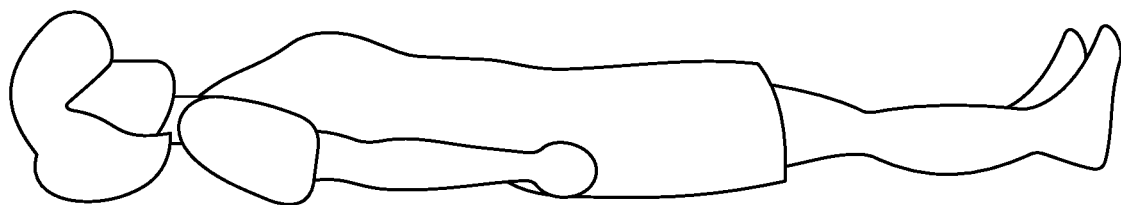
Supine
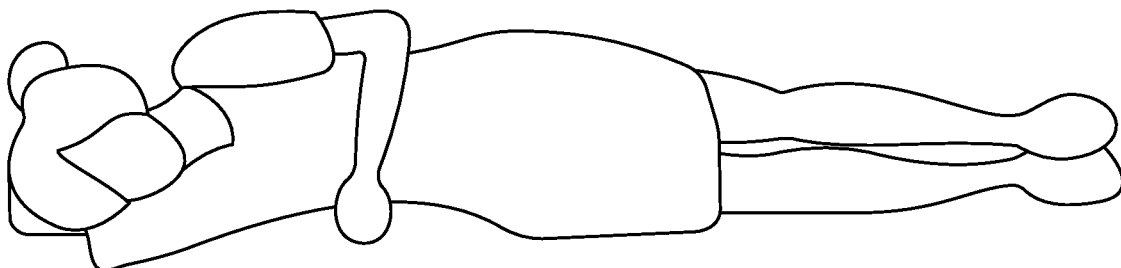
Right Lateral Recumbent
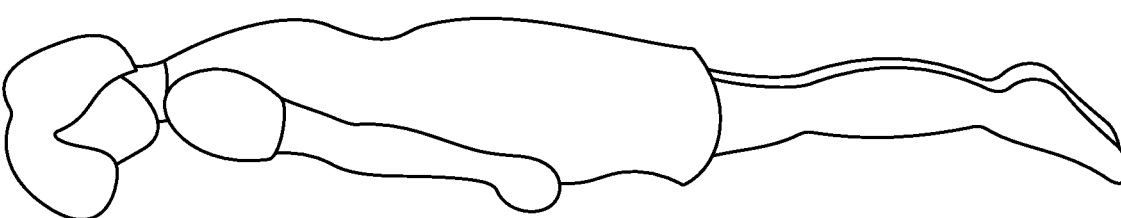
Prone
FIG. 2F

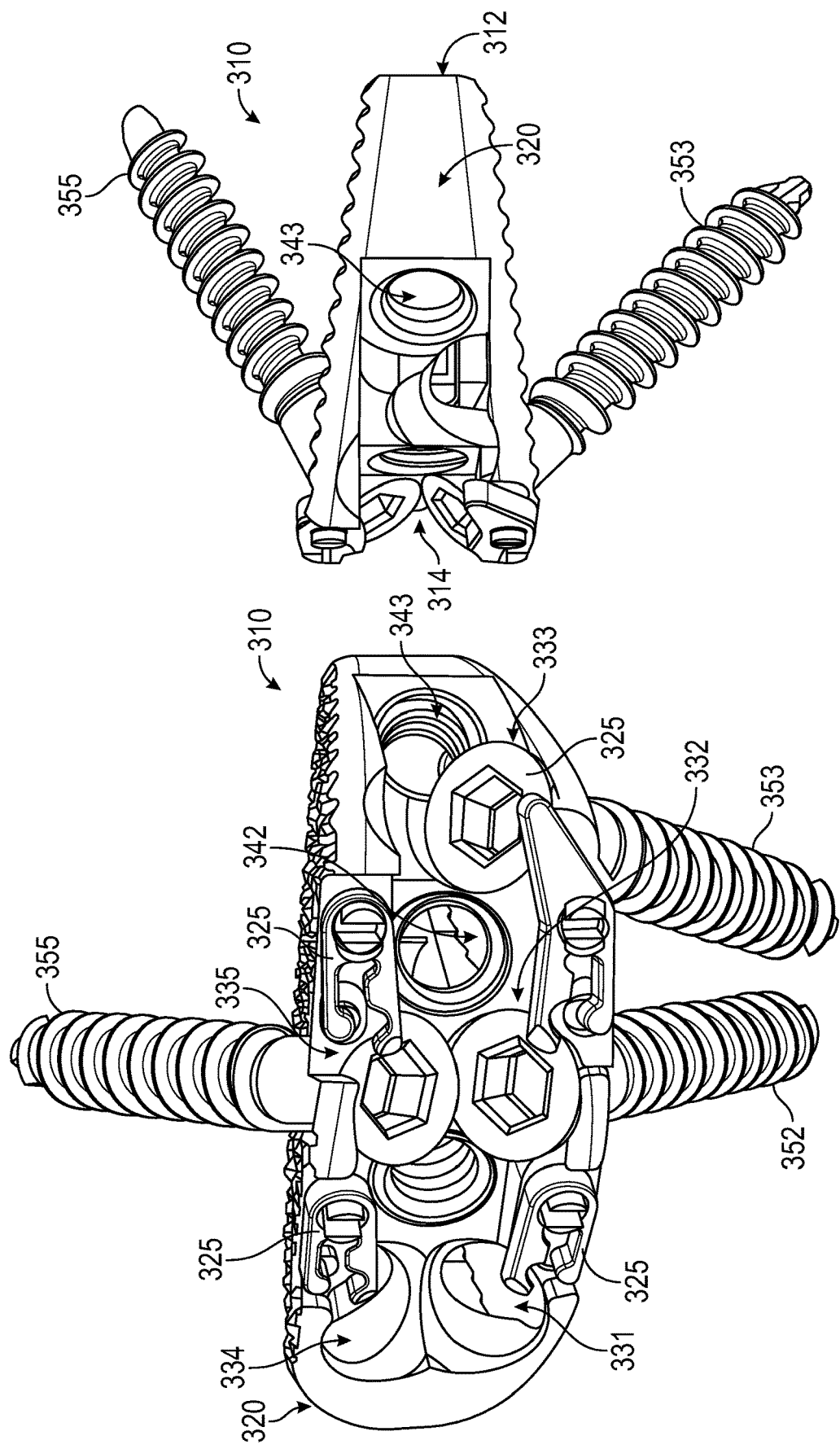

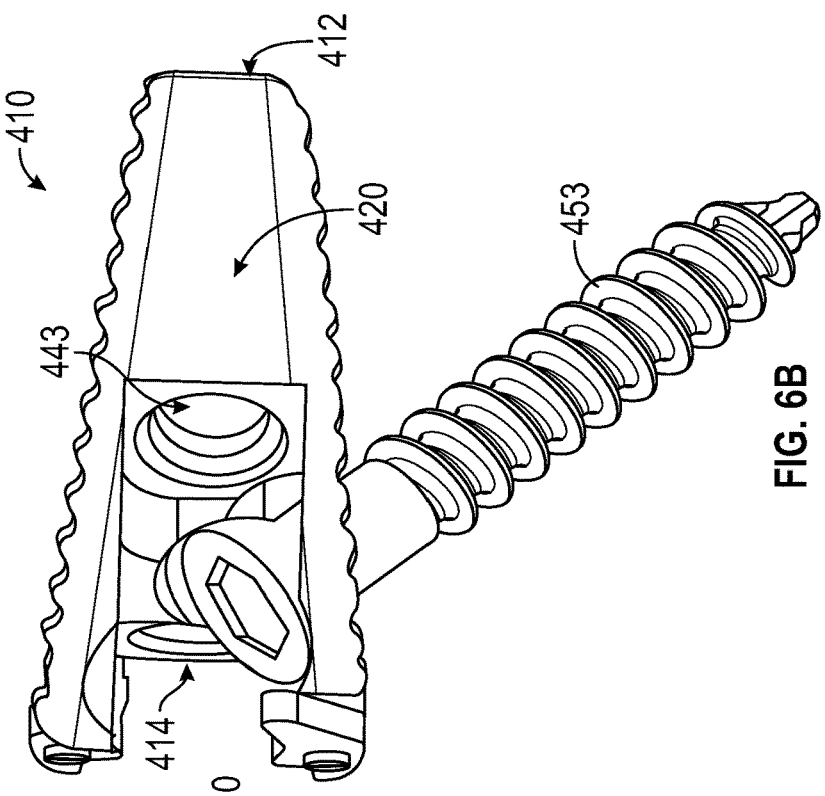
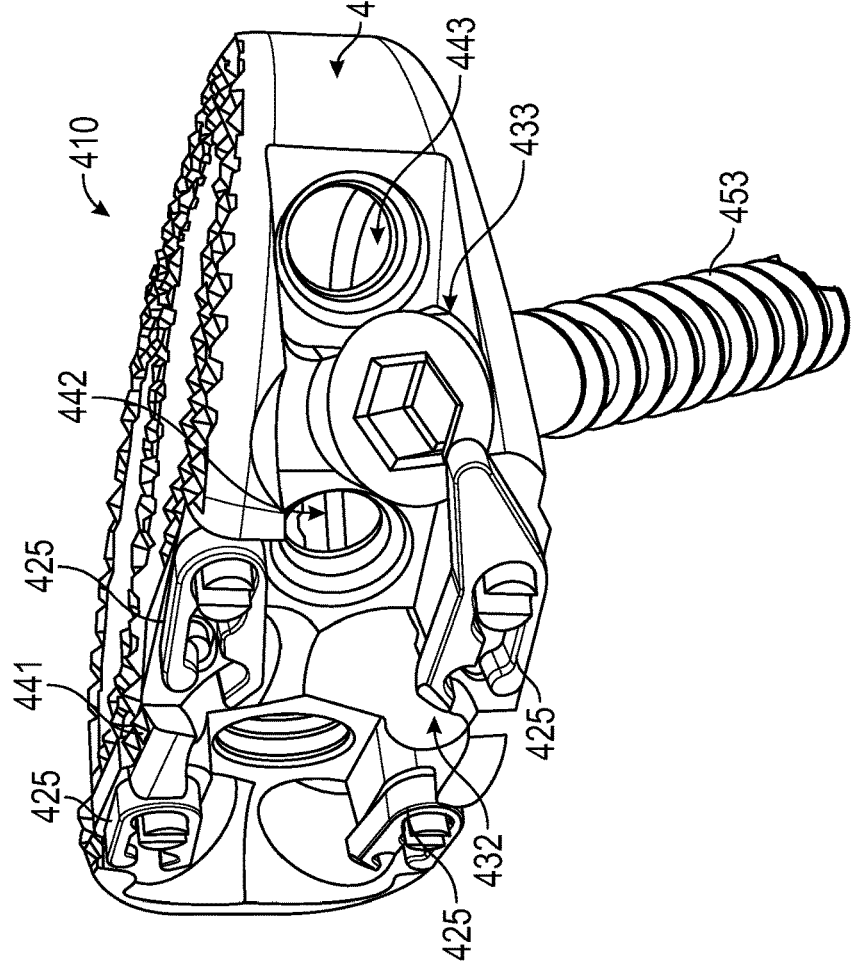
FIG. 6B
FIG. 6A

INTERBODY CAGE DEVICE AND METHODS OF USE

CROSS REFERENCE TO RELATED APPLICATION

This application is a continuation of U.S. patent application Ser. No. 17/444,084, filed Jul. 30, 2021, which claims the benefit of the filing date of U.S. Provisional Patent Application No. 63/059,160, filed Jul. 30, 2020. The aforementioned applications are incorporated herein by reference in their entirety for all purposes.

FIELD OF THE INVENTION

The present disclosure generally relates to implants used in spinal surgical procedures in a human. More particularly, the disclosure generally relates to implants used for implant and/or fusion and its methods of use and implantation approach.

BACKGROUND OF THE INVENTION

The treatment of disorders to the spine has advanced over the years to be adapted to to address many forms of spinal disorders. Multiple surgical approaches exist to treat spinal disorders, including Anterior Lumbar Interbody Fusion (a.k.a. ALIF), Oblique Lumbar Interbody Fusion/Anterior to Psoas (a.k.a. OLIF/ATP) and Direct Lateral Interbody Fusion/Extreme Lateral Interbody Fusion (a.k.a. DLIF, XLIF), to name a few. However, with each approach to the spine, a different implant is required.

In addition, there presently exists no method of selecting the size of an interbody fusion device which enables a controlled decompression of the nerves and restoration of the proper spinal alignment.

In addition, there presently exists no method of approaching the spine of a patient for spinal interbody fusion or total disc replacement through the oblique corridor which enables the patient to be positioned on the operating table in the supine position.

BRIEF DESCRIPTION OF THE DRAWINGS

Examples illustrative of embodiments of the disclosure are described below with reference to figures attached hereto. In the figures, identical structures, elements or parts that appear in more than one figure are generally labeled with the same numeral in all the figures in which they appear. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings. The figures (FIGS.) are listed below.

FIG. 2F shows exemplary supine, right lateral recumbent, and prone positions of an exemplary patient.

FIGS. 5A-5B shows a fourth embodiment of an implant which may be used with the Supine ATP approach illustrating an exemplary screw use of the implant.

FIGS. 6A and 6B show a fifth embodiment of an implant which may be used with the Supine ATP approach illustrating an exemplary screw use of the implant.

It should be clear that the description of the embodiments and attached figures set forth in this specification serves only for a better understanding, without limiting scope. It should also be clear that a person skilled in the art, after reading the present specification could make adjustments or amendments to the attached figures and above described embodiments that would still be covered by the present disclosure.

DETAILED DESCRIPTION OF INVENTION

This disclosure describes medical devices for use in spinal surgical procedures, and across multiple spinal surgical approaches. Additionally, this disclosure provides methods for selecting the appropriate sizing of such medical devices to be used in inventive surgical approaches.

It is to be understood the present disclosure is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an', and "the" include singular and plural referents unless the content clearly dictates otherwise.

Unless defined otherwise, all technical and scientific terms used herein have the same meaning as commonly understood by one of ordinary skill in the art.

The phrase "ATP", as used herein, generally refers to a surgical pathway or spinal entry point that is anterior to the psoas muscle in a subject including, but not limited to, the pathway anterior to the psoas muscle in the abdomen and/or a retroperitoneal approach to the spine in the abdomen. Generally, the ATP skin incision point is more medial than an oblique skin incision point.

The phrase 'AL", as used herein, generally refers to the surgical pathway that is lateral to a direct anterior-midline surgical pathway in a subject including, but not limited to the retroperitoneal pathway to the spine in the abdomen.

The phrase 'cage', as used herein, generally refers to a spacer (a.k.a. "interbody", "intervertebral implant", "interbody fusion device") implant or bone graft that is positioned between adjacent vertebrae during spinal surgery.

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

Figure 1A:
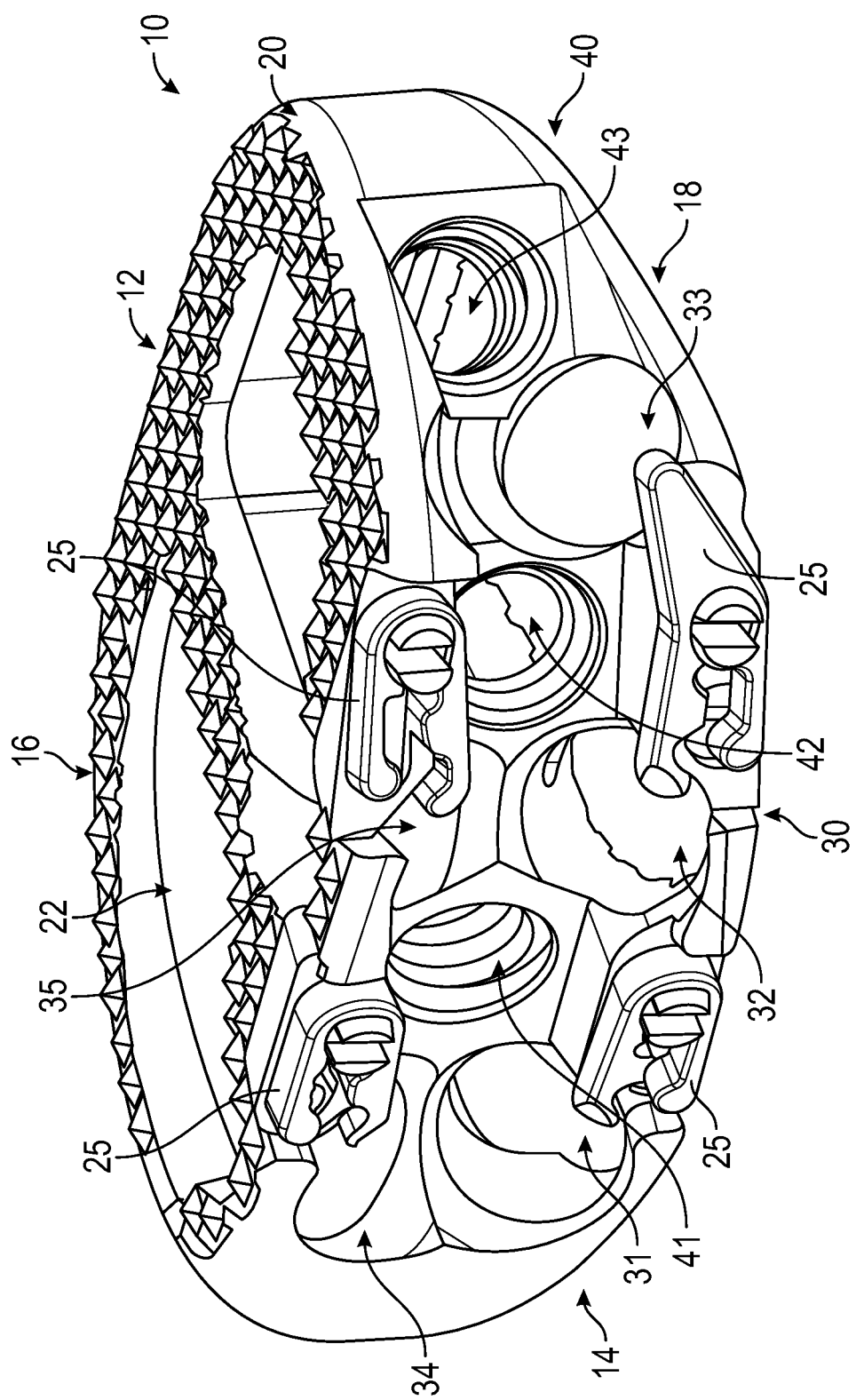
FIGS. 1A-C show a first embodiment of an exemplary implant.
Figure 1B:
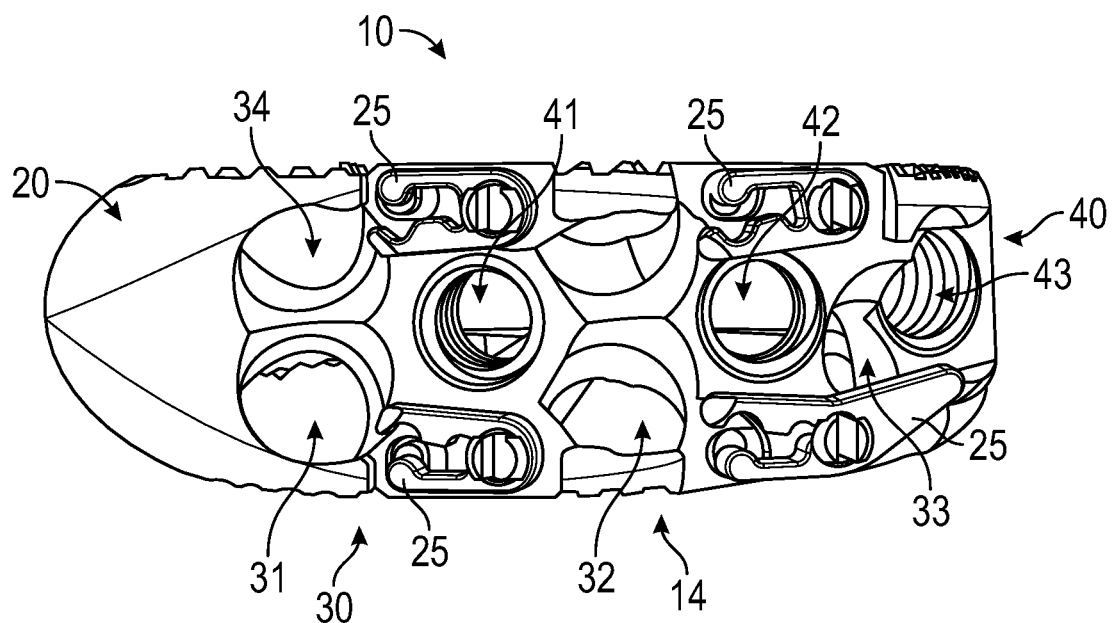
Figure 1C:
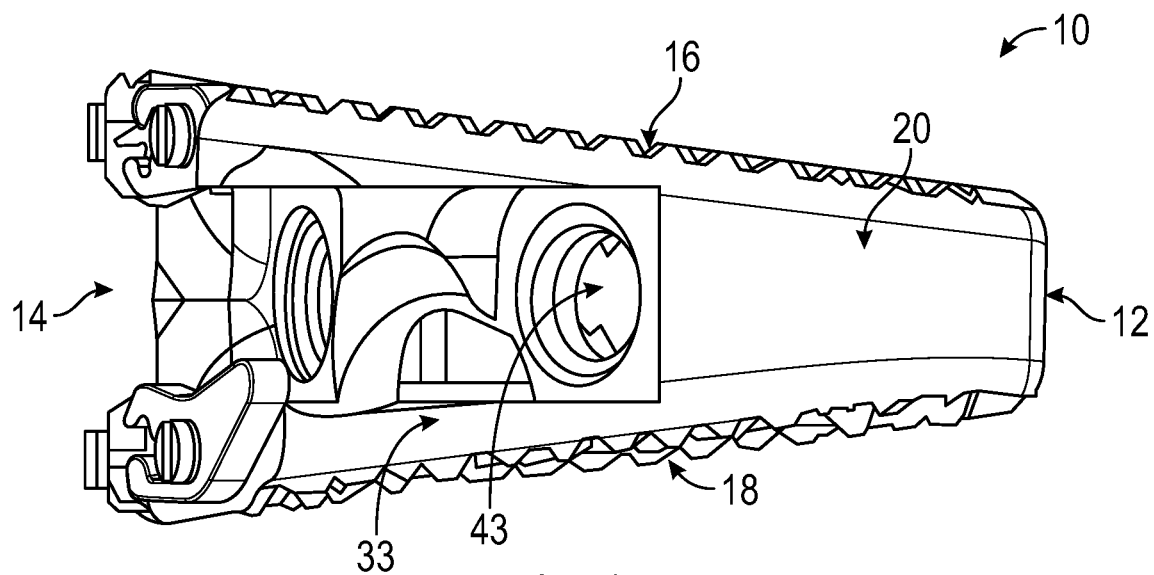

The present disclosure provides for a spinal interbody fusion device for use in a plurality of spinal surgical approaches. The device includes an interbody cage which is substantially oval and substantially hollow, having two sides representing width and two sides representing length of the cage. A first embodiment of the cage is illustrated in FIGS. 1A, 1B, and 1C. As shown in FIGS. 1A, 1B, and 1C an interbody cage 10, includes a back 12, front 14, top 16, and bottom 18. Also shown in FIGS. 1A and 1B are clips 25. The cage 10 includes two or more holes along its outer surface 20, which travel through all or a portion of the cage 10 into an interior 22. In the first exemplary embodiment as shown in FIGS. 1A, 1B, and 1C, the cage 10 includes at least one hole 30, 40 on one side representing a width, and at least one hole 30, 40 on one side representing a length. Placement of at least one hole 30, 40 in these locations allow for use of the implant device in multiple approaches using the same device (here cage 10). Each hole 30, 40 is configured for accepting a screw or anchor and one or more hole is accessible for one or more surgical approaches for performing a spinal fusion, including, without limit, Anterior Lumbar Interbody Fusion (ALIF), Anterior Lateral Anterior Lumbar Interbody Fusion (AL-ALIF), Anterior to Psoas (ATP), Supine-ATP, Supine-Oblique, and Oblique, to name a few. As shown in FIGS. 1A, 1B, and 1C, holes 30 include holes 31, 32, 34, and 35 that can act as fixation holes, which are shown on the implant width side that can accept a screw or anchor and hole 33 that can act as a fixation hole, which is shown on the implant length side that can accept a screw or anchor and holes 41, 42, and 43 that can act as inserter holes, with hole 41 generally indicating an ALIF inserter hole, hole 42 generally indicating an AL-ALIF inserter hole, and hole 43 generally indicating a Supine ATP and Supine Oblique inserter hole. FIG. 1B generally shows an interbody width view and FIG. 1C generally shows an implant length view.

Figure 1D:
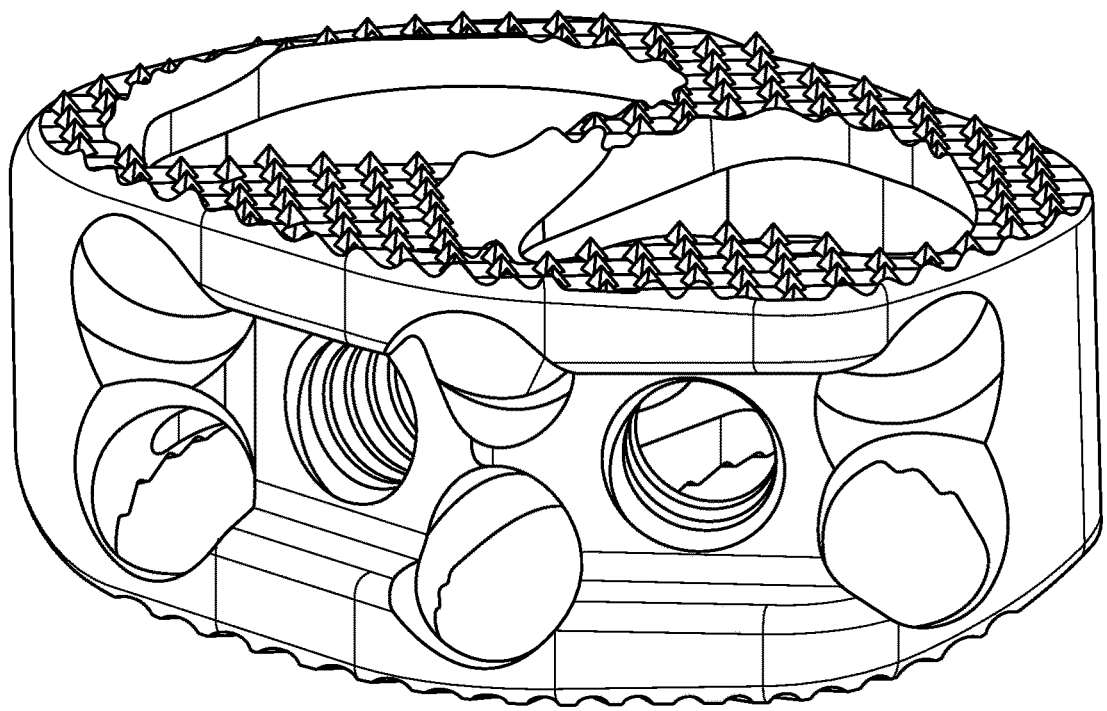
FIGS. 1D-F show a second embodiment of an exemplary implant.
Figure 1E:
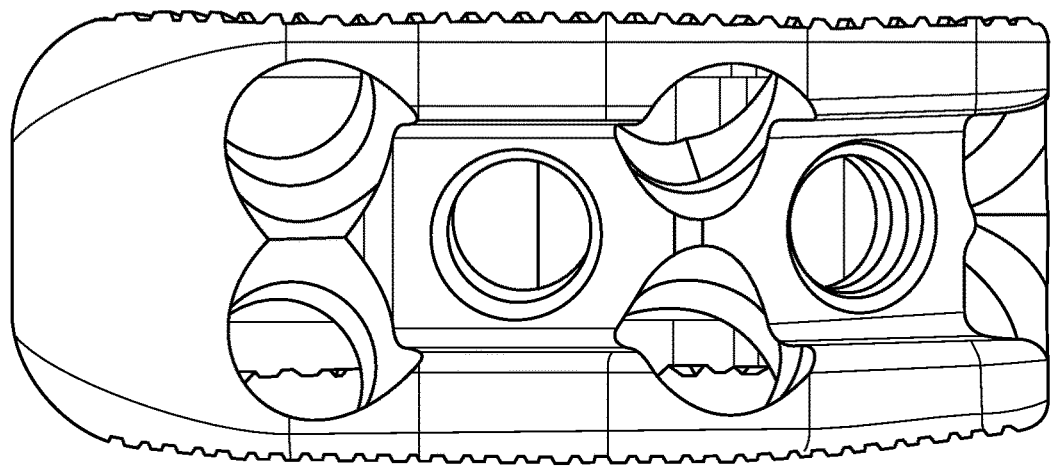
Figure 1F:
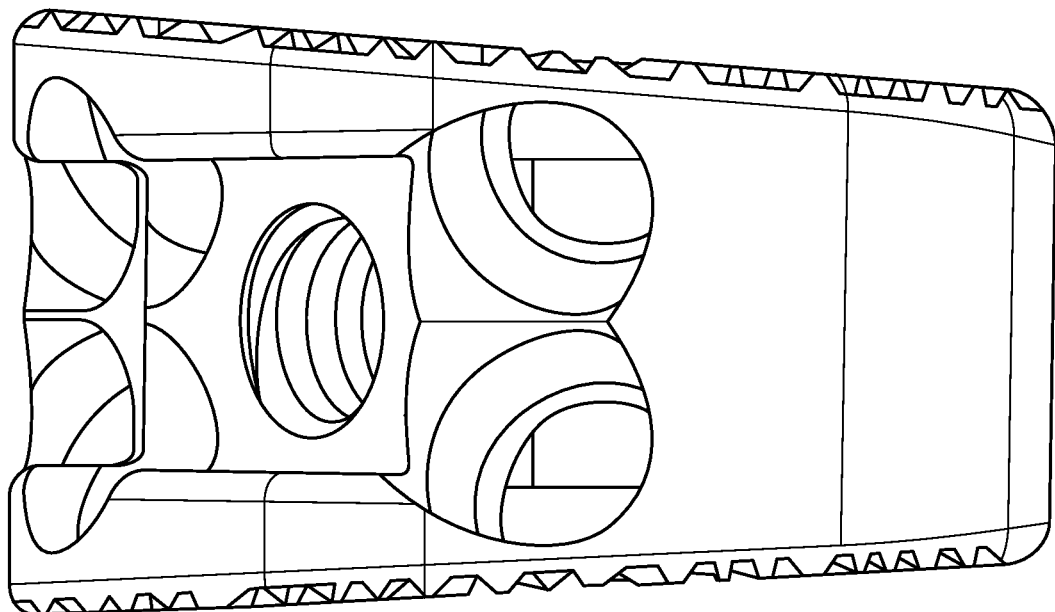

A second embodiment of the cage is illustrated in FIGS. 1D, 1E, and 1F. Although the second embodiment shown in FIGS. 1D, 1E, and 1F includes substantially similar features to the first embodiment, the second embodiment includes six available exemplary screw holes.

Figure 1G:
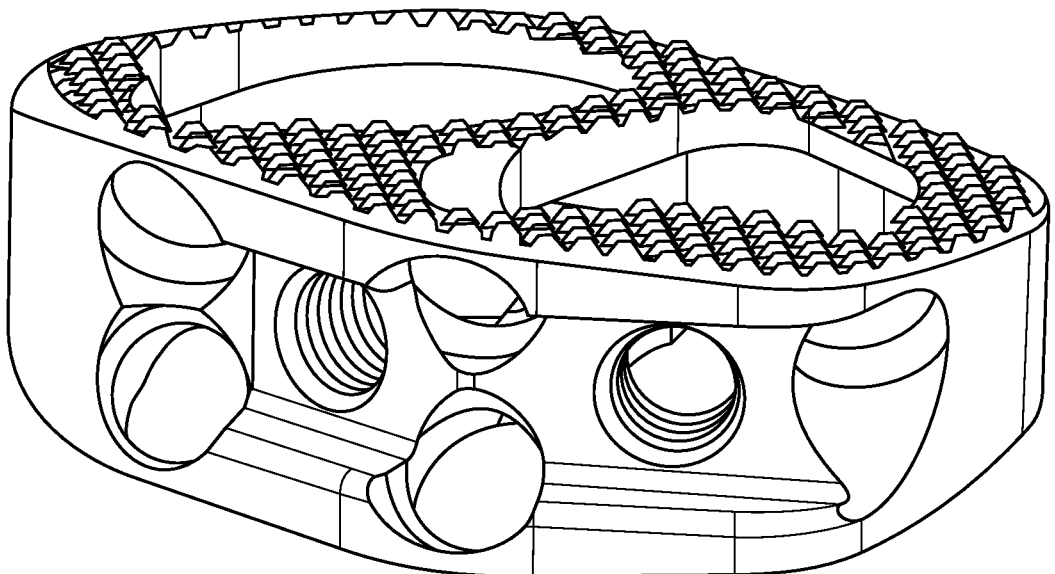
FIGS. 1G-I show a third embodiment of an exemplary implant.
Figure 1H:
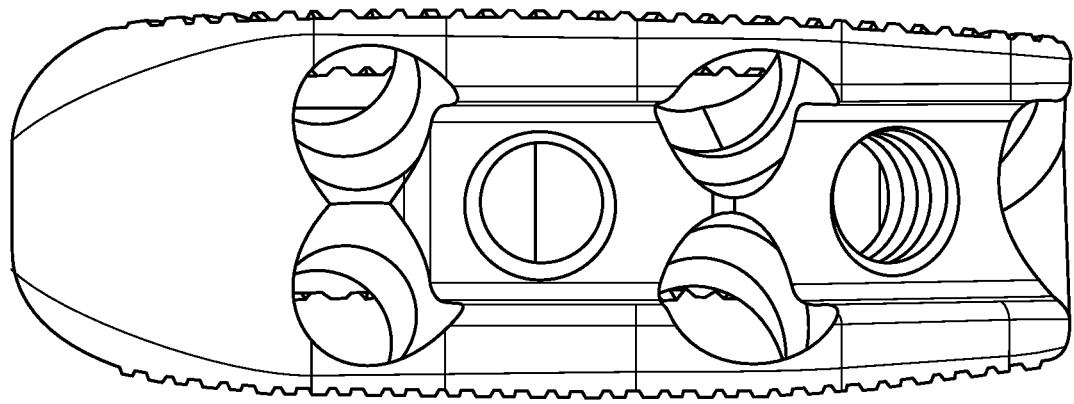
Figure 1I:
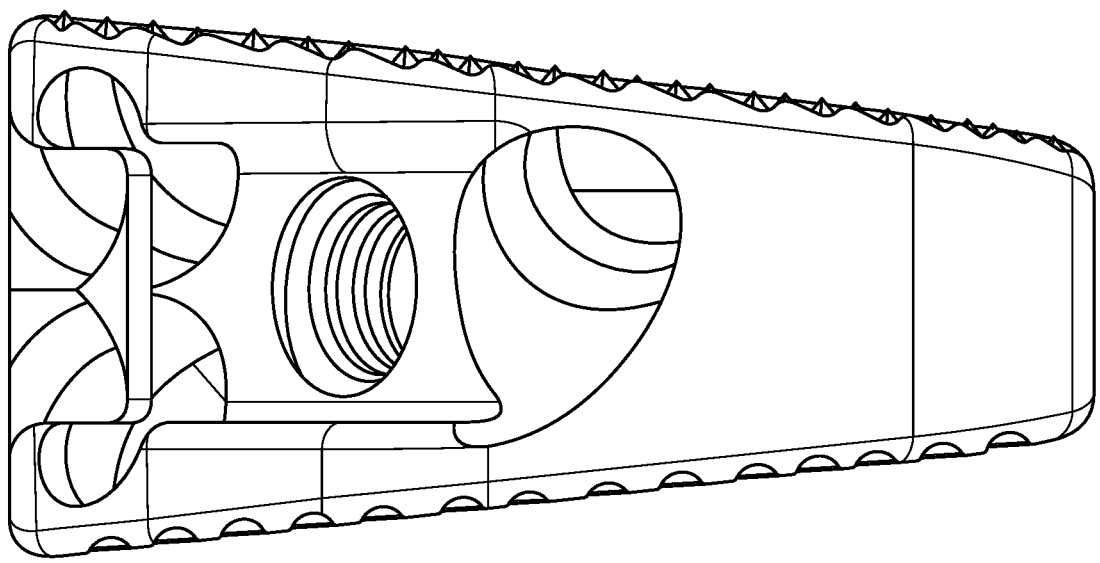

A third embodiment of the cage is illustrated in FIGS. 1G, 1H, and 1I. Although the third embodiment shown in FIGS. 1G, 1H, and 1I includes substantially similar features to the first and second embodiments, the third embodiment includes two inserter hole with five available exemplary screw holes.

Figure 2A:
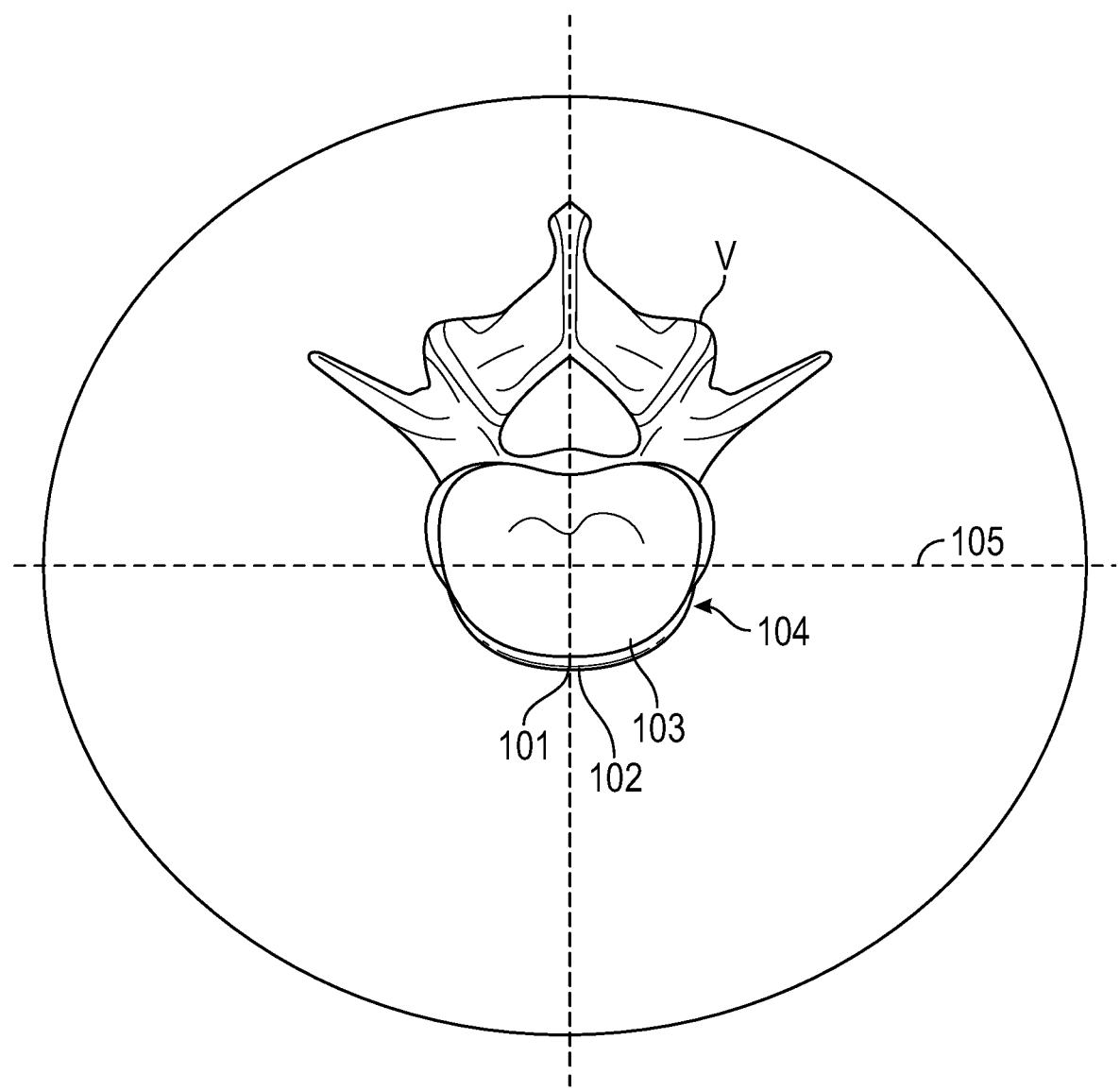
FIG. 2A shows an exemplary orientations of ALIF, AL-ALIF and Supine ATP surgical approaches relative to a Subject's vertebrae.

FIG. 2A shows exemplary orientations of ALIF at 101, AL-ALIF at 102, and ATP, Supine-ATP, and Supine-Oblique at 103 and 104 surgical approaches relative to a Subject's vertebrae V. An exemplary right/left axis in the transverse plane is also shown at 105.

Figure 2D:
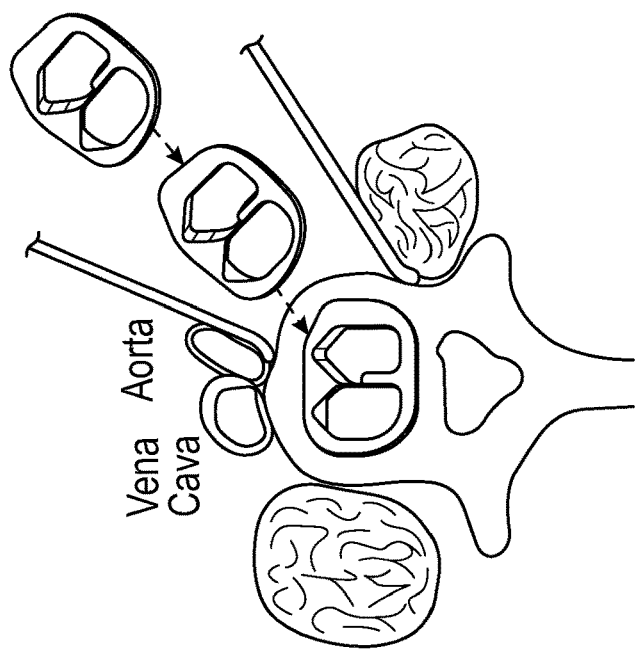
FIGS. 2B through 2D show exemplary approaches for the exemplary implants shown in FIGS. 1A through 1I to be inserted.
Figure 2C:
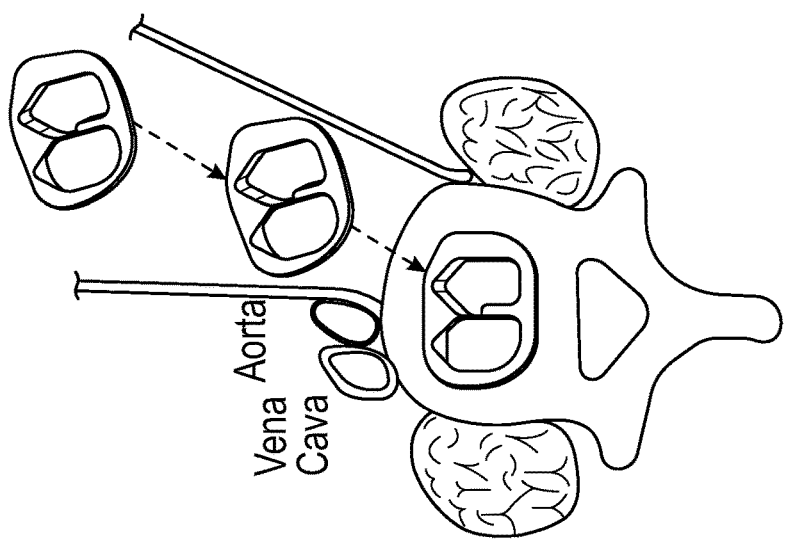
Figure 2B:
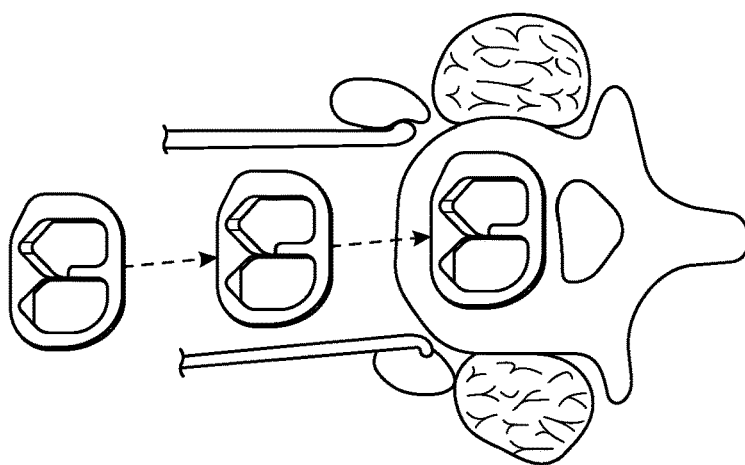
Figure 2E:
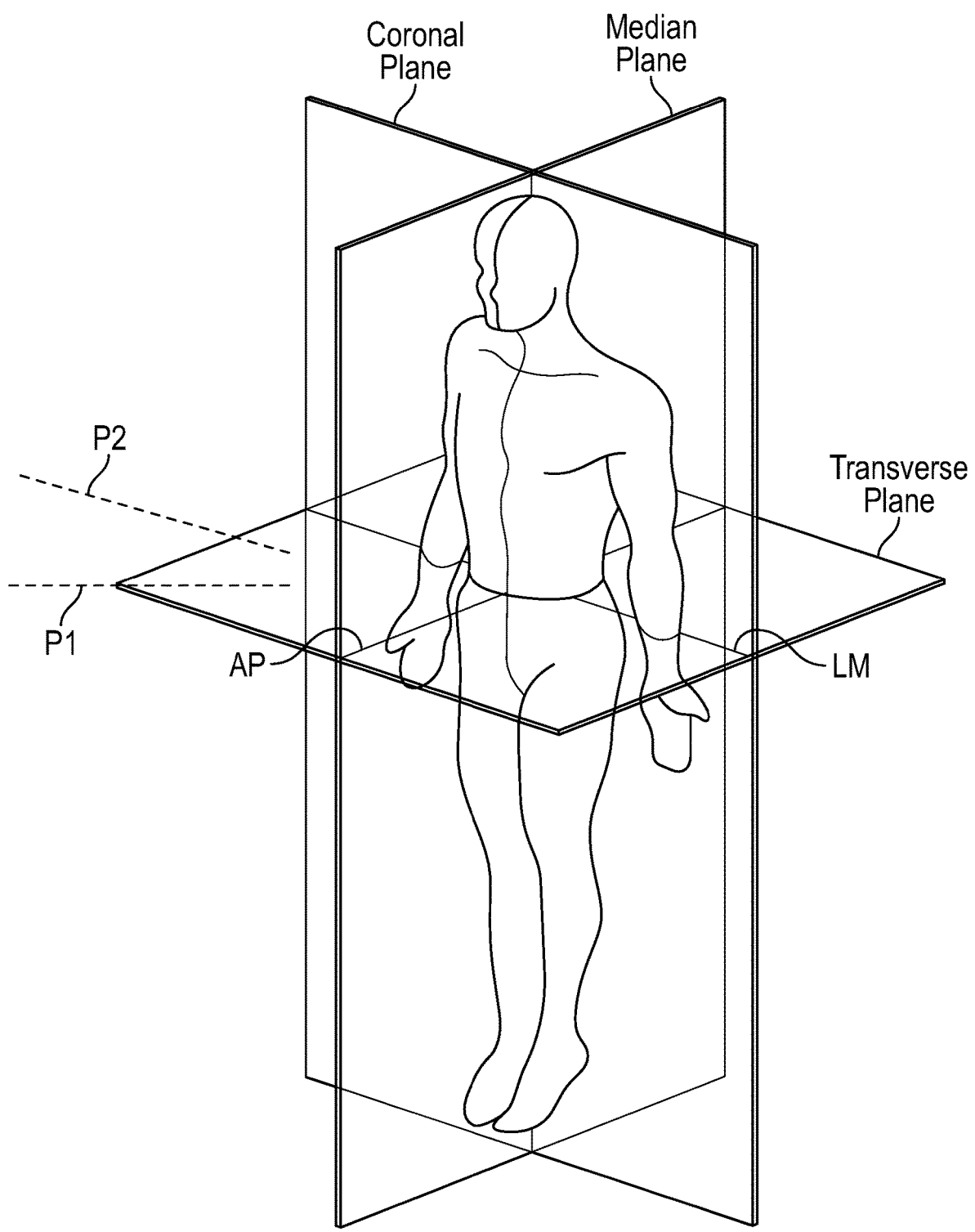
FIG. 2E illustrates body planes showing a patient and exemplary axes.
Figure 2G:
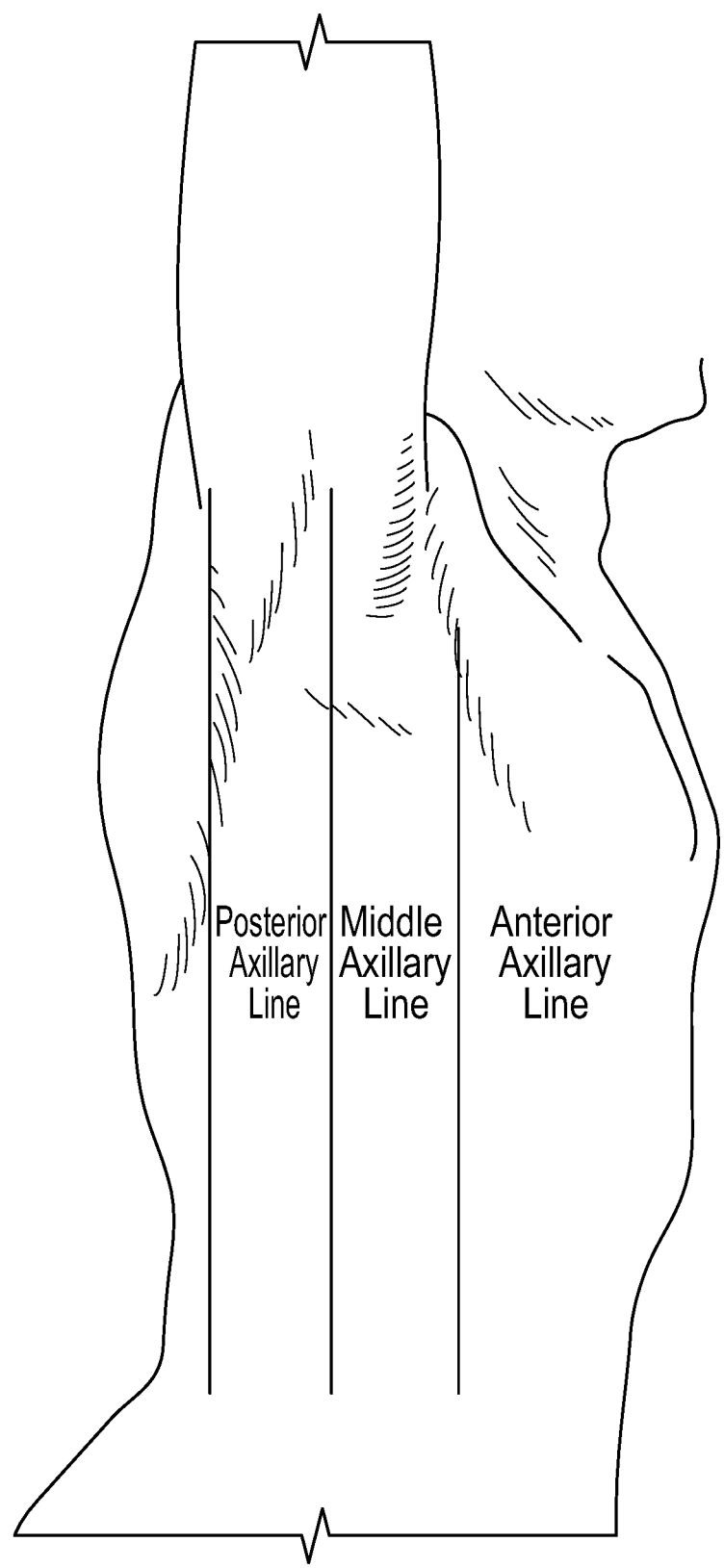
FIG. 2G shows a posterior auxiliary line, middle auxiliary line, and anterior auxiliary line of an exemplary subject.

FIGS. 2B through 2D show exemplary approaches for the exemplary implants shown in FIGS. 1A through 1I to be inserted. FIG. 2E illustrates body planes showing a patient with exemplary axes. FIG. 2F shows exemplary supine, right lateral recumbent, and prone positions of an exemplary patient. FIG. 2G shows a posterior auxiliary line, middle auxiliary line, and anterior auxiliary line of an exemplary subject.

Exemplary embodiments detailed herein allow for multiple uses of the interbody fusion device. Uses of the exemplary devices include as a lumbar cage implant across a plurality of surgical approaches including, without limit anterior, anterior-lateral, oblique, anterior to psoas, lateral, or combinations thereof.

Figure 3B:
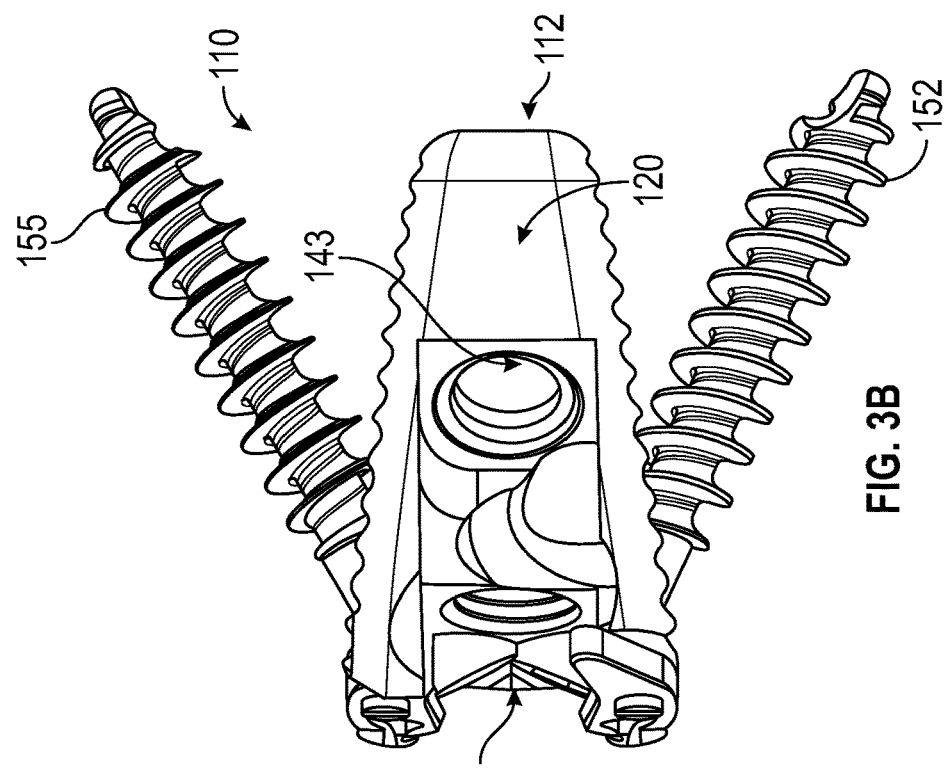
FIGS. 3A and 3B show a second embodiment of an implant which may be used with the ALIF approach illustrating an exemplary screw use of the implant.
Figure 3A:
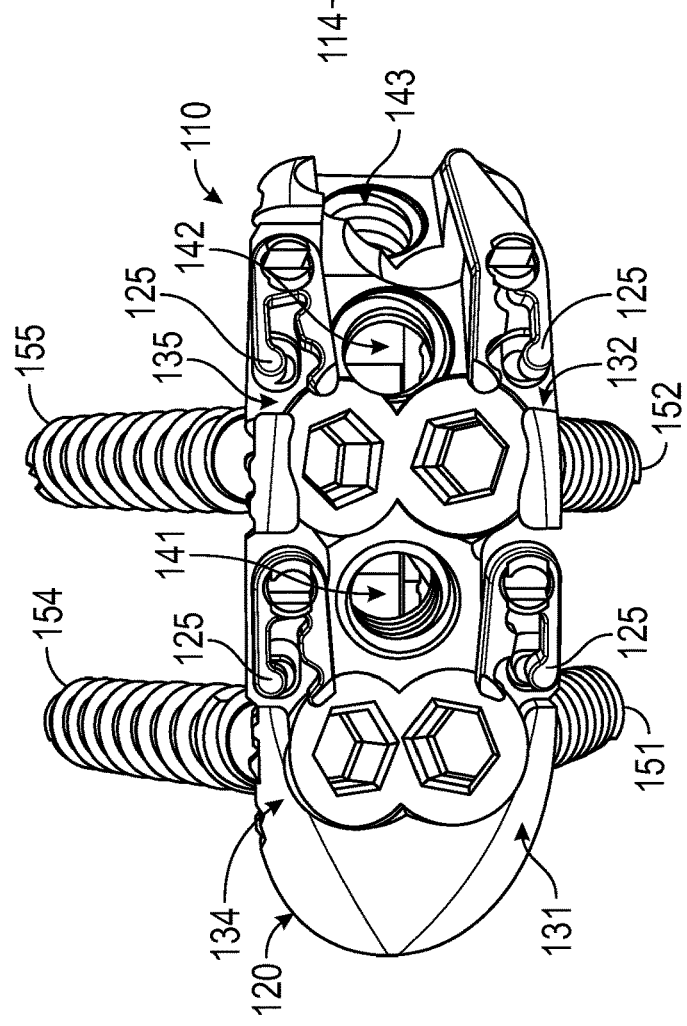

FIGS. 3A and 3B show a second embodiment of an implant which may be used with the ALIF approach illustrating an exemplary screw use of the implant. The implant 110 shown in FIGS. 3A and 3B includes a back 112, front 114, and outer surface 120. Exemplary screws are shown in fixation holes 131, 132, 134, and 135, with screw 151 in hole 131, screw 152 in hole 132, screw 154 in hole 134, and screw 155 in hole 135. Inserter holes 141, 142, and 143 and clips 125 are also shown in FIGS. 3A and 3B.

Figure 4A:
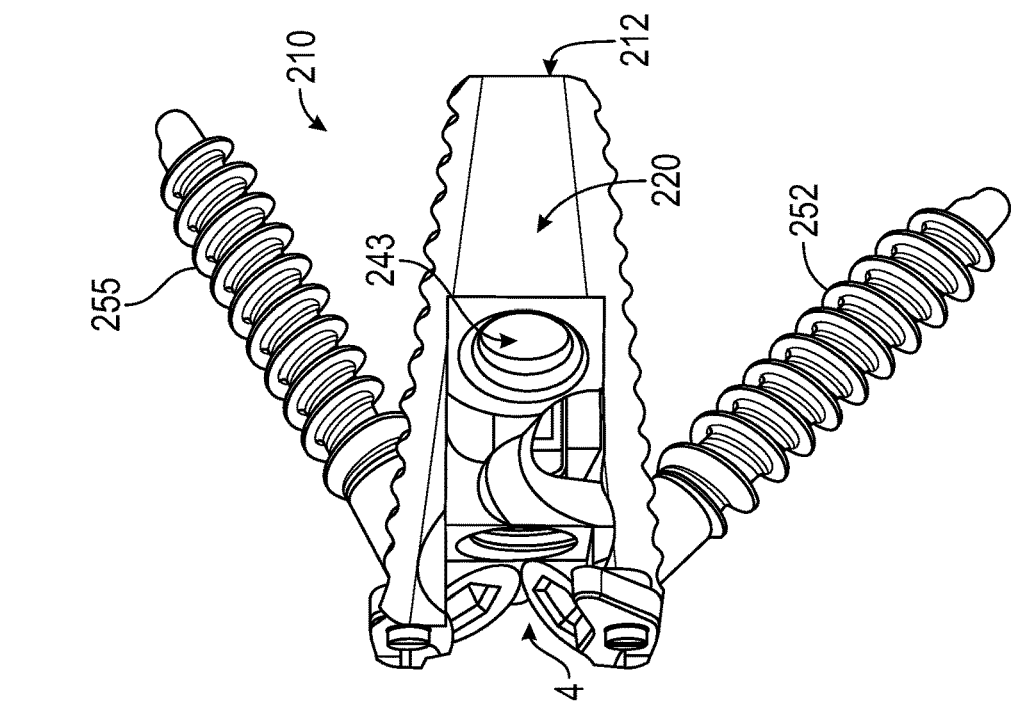
FIGS. 4A and 4B show a third embodiment of an implant which may be used with the AL-ALIF approach illustrating an exemplary screw use of the implant.
Figure 4B:
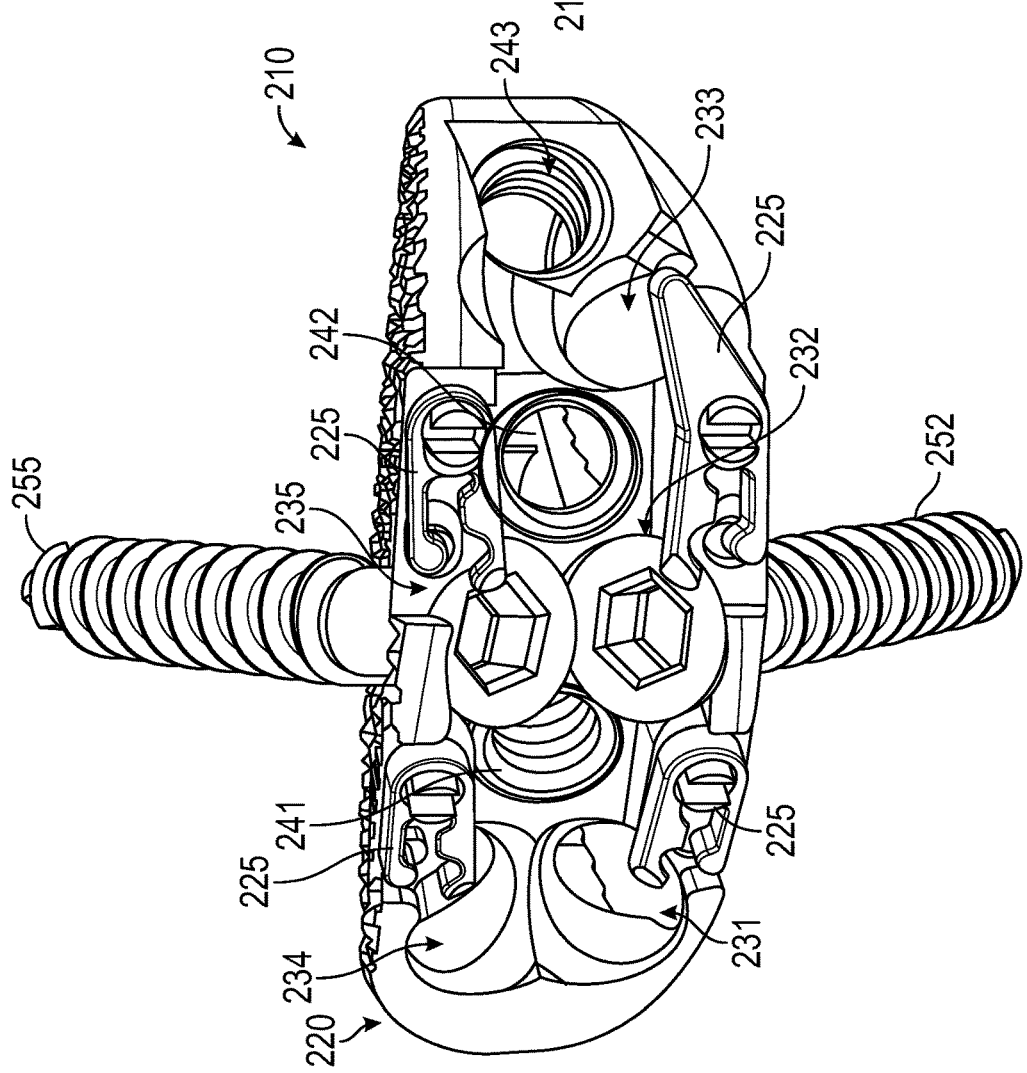

FIGS. 4A and 4B show a third embodiment of an implant which may be used with the AL-ALIF approach illustrating an exemplary screw use of the implant. The implant 210 shown in FIGS. 4A and 4B includes a back 212, front 214, and outer surface 220. Exemplary screws are shown in fixation holes 232 and 235, with screw 252 in hole 232 and screw 255 in hole 235. Inserter holes 241, 242, and 243 and clips 225 are also shown in FIGS. 4A and 4B.

FIGS. 5A and 5B show a fourth embodiment of an implant which may be used with the Supine ATP approach illustrating one embodiment of the screw use of the implant for that approach. The implant 310 shown in FIGS. 4A and 4B includes a back 312, front 314, and outer surface 320. Exemplary screws are shown in fixation holes 332, 333, and 335, with screw 352 in hole 332 screw 353 in hole 333, and screw 355 in hole 335. Inserter holes 341, 342, and 343 and clips 325 are also shown in FIGS. 5A and 5B.

FIGS. 6A and 6B show a fifth embodiment of an implant which may be used with the Supine ATP approach illustrating an exemplary screw use of the implant. The implant 410 shown in FIGS. 6A and 6B includes a back 412, front 414, and outer surface 420. An exemplary screw 453 is shown in fixation hole 433. Inserter holes 441, 442, and 443 and clips 425 are also shown in FIGS. 6A and 6B.

Figure 7:
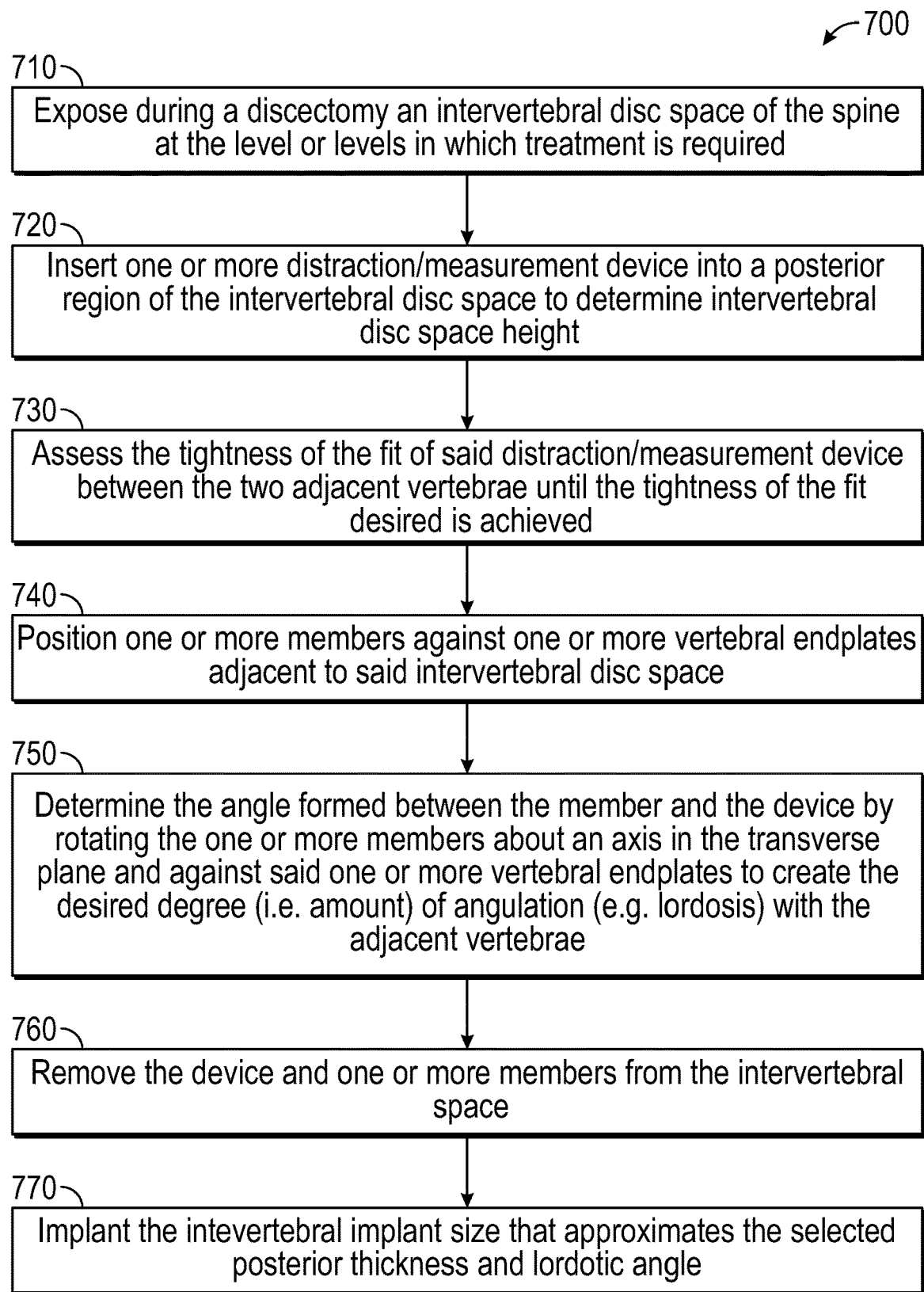
FIG. 7 shows an exemplary method of selecting a size of an intervertebral implant.

FIG. 7 shows an exemplary method of selecting a size of an intevertebral implant with the goal of improving the surgical outcome such as: reduced pain and/or improved spinal alignment. The method 700 shown in FIG. 7 includes step 710 where an intervertebral disc space 500 is exposed during a discectomy at the level or levels in which treatment is required. Then, at step 720, one or more distraction/measurement device(s) 501 is/are inserted into a posterior region 502 of the intervertebral disc space 500 to determine intervertebral disc space height H. At step 730, the fit of the distraction/measurement device 501 is assessed between the two adjacent vertebrae V1, V2 until the fit desired is achieved. At step 740, one or more members 503, 504 is/are positioned against one or more vertebral endplates adjacent to the intervertebral disc space. At step 750, the angle A formed between the member and the device is determined by rotating the one or more members about an axis in the transverse plane and against the one or more vertebral endplates to create the desired degree (i.e., amount) of angulation (e.g., lordosis) with the adjacent vertebrae. At step 760, the device and one or more members is/are removed from the intervertebral space. At step 770, the intervertebral implant size that approximates the selected posterior height and lordotic angle is implanted.

Figure 8A:
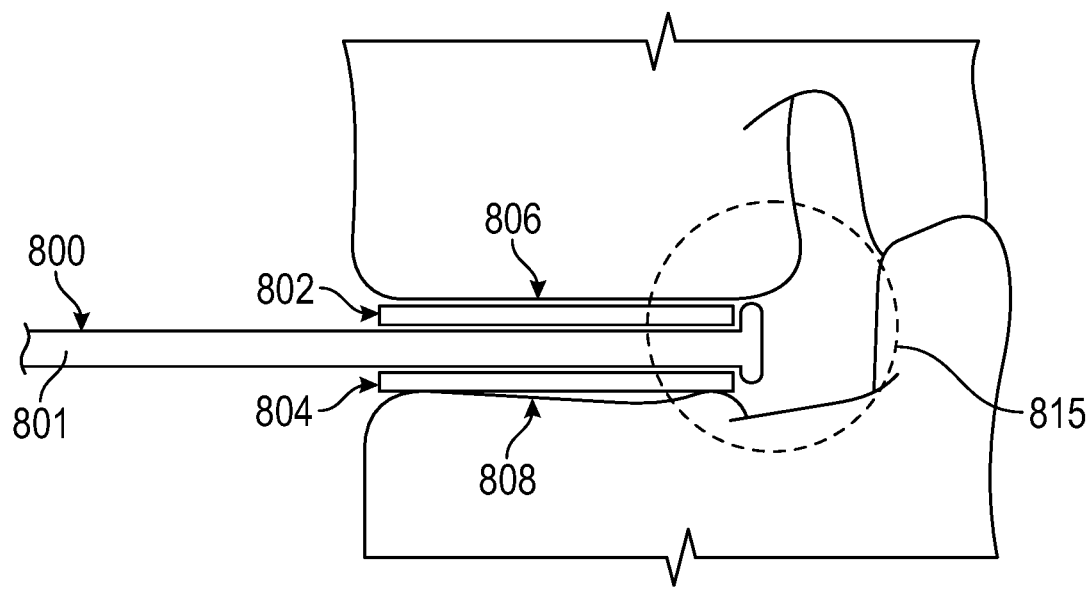
FIGS. 8A, 8B, and 8C show an exemplary embodiment of instrumentation which may be used with the method of selecting the size of an intervertebral implant.
Figure 8B:
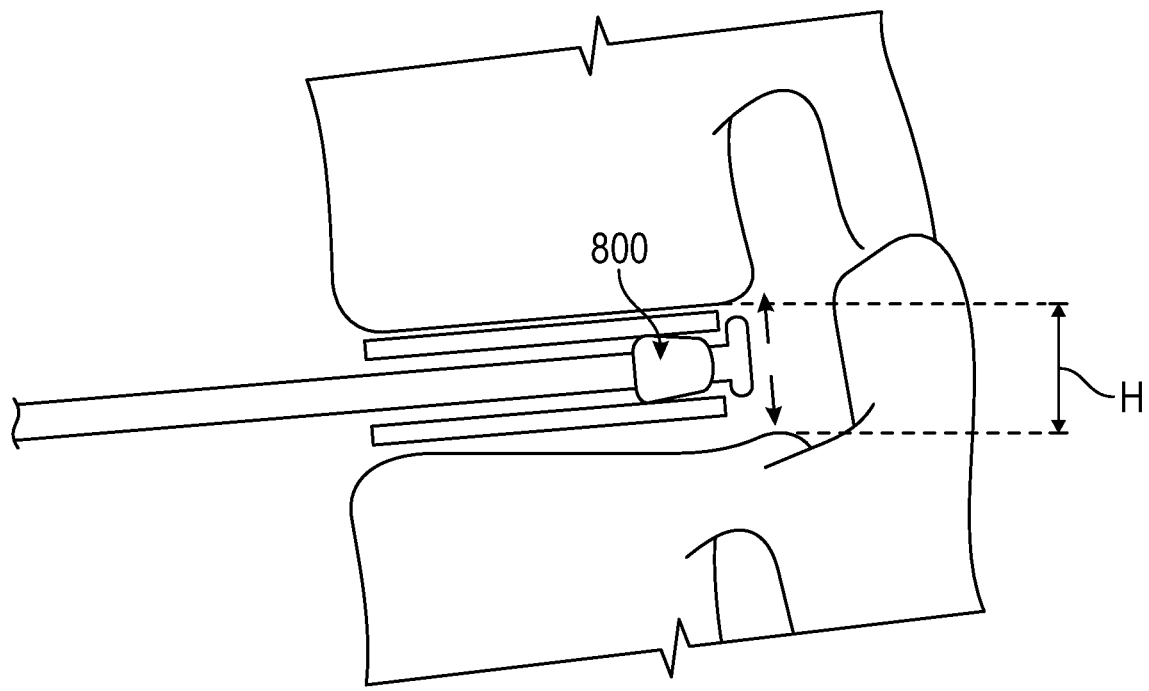
Figure 8C:
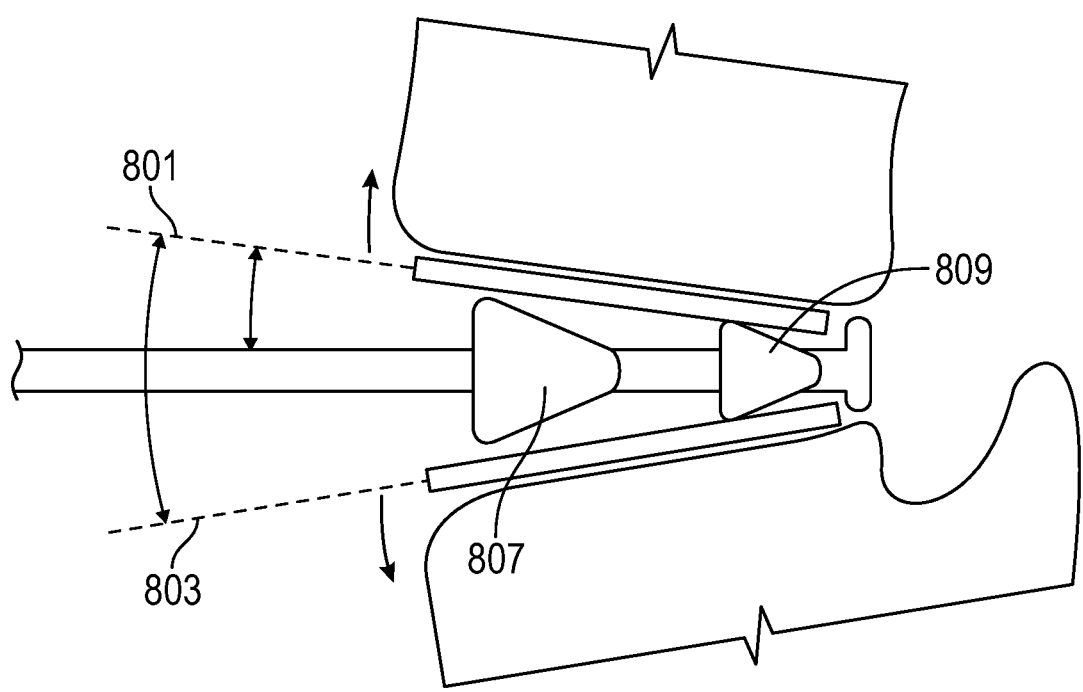

FIGS. 8A, 8B, and 8C show an exemplary embodiment of a distraction measuring device 800 which may be used with the method of selecting the size of an intevertebral implant. As shown in FIG. 8A, a shaft that receives the posterior distraction/sizing member and the anterior distraction/sizing member is shown at 801, a first member 802 is disposed adjacent vertebral endplate 806 and a second member 804 is disposed adjacent vertebral endplate 808. Also shown at 815 is the posterior region of intervertebral disc space. In FIG. 8B, distracting/measuring device 800 is shown with disc space height H of the posterior region. The trapezoidal member slides over the shaft of member 801. In at least one instance, multiple posterior height trapezoidal members can be available for a surgeon to use, with the members acting like 'feeler gauges' to enable the surgeon to titrate or determine the proper posterior height. The assessment of the proper posterior height will generally be based on: 1) tightness of fit and 2) observation of foraminal decompression as seen on X-ray.

As shown in an exemplary configuration in FIGS. 8A, 8B, and 8C, the end of member 801 is in the shape of a T. One purpose of the T shape is to prevent the trapezoidal member from being pushed into the spinal cord. In FIG. 8C, member-device angle 801, angulation between adjacent vertebrae (e.g. lordosis) at 803 (a.k.a. lordotic angle), anterior distraction/sizing member 807, and posterior distraction/sizing member 809 are shown. The anterior height trapezoidal member, 807, slides over the shaft of member 801. In at least one instance, multiple anterior height trapezoidal members can be available for a surgeon to use, with the members acting like 'feeler gauges' to enable the surgeon to titrate or determine the proper anterior height and, in combination with the posterior trapezoidal member, 809, and the distance between the two, the lordotic angle. The assessment of the proper anterior height and lordotic angle generally will be based on: 1) tightness of fit and 2) observation of the spinal curvature in the sagittal plane. One exemplary method involving FIGS. 8A, 8B, and 8C includes: (1) Approach spine, (2) Complete discectomy and disk prep, (3) Insert 801 into the intervertebral disc space so that the distal T-end is in the posterior region of the intervertebral space, (4) Insert the 802 and 804 plates, (5) Assemble 800 to 801 at the proximal end of 801 and translate 800 on 801 in the distal direction (i.e. toward the T-end of 801 at the posterior region of the intervertebral disc space), (6) As 800 engages plates: 802 and 804, these plates cause vertebrae 806 and 808 to increase their separation distance. In addition, the foraminal openings in the posterior spine may increase and decompress the adjacent nerves, (7) The surgeon assesses the degree of separation and foraminal opening using X-ray, (8) In the event the selected distraction wedge (i.e. 800) does not provide sufficient separation of vertebrae 806 and 808, then the selected wedge is removed or augmented so that a larger distraction wedge is positioned between 802 and 804 and steps "5", "6" and "7" are repeated until the desired vertebrae separation, and possibly the desired foraminal opening, is/are observed/obtained. The final distraction wedge size is recorded, (9) Assemble 807 to 801 at the proximal end of 801 and translate 807 on 801 in the distal direction (i.e. toward the anterior region of the intervertebral disc space), (10) As 807 engages plates 802 and 804, these plates cause vertebrae 806 and 808 to increase their separation distance and possibly their relative rotation about axes that are generally in the transverse plane for each vertebrae which affects the alignment of the spine in the sagittal plane with a net effect of affecting the patient's degree of lordosis, (11) The surgeon assesses the patient's sagittal plane alignment using X-ray, (12) In the event the selected distraction wedge (i.e. 807) does not provide sufficient angular rotation of vertebrae 806 and 808, then the selected wedge is removed or augmented so that a larger distraction wedge is positioned between 802 and 804 and steps "9", "10" and "11" are repeated until the desired degree of lordosis is observed/obtained, The final distraction wedge size is recorded, (13) All components of the instrument are removed from the intervertebral disc space, and (14) A intervertebral implant with a posterior and anterior height that matches the recorded sizes is implanted.

Figure 9:
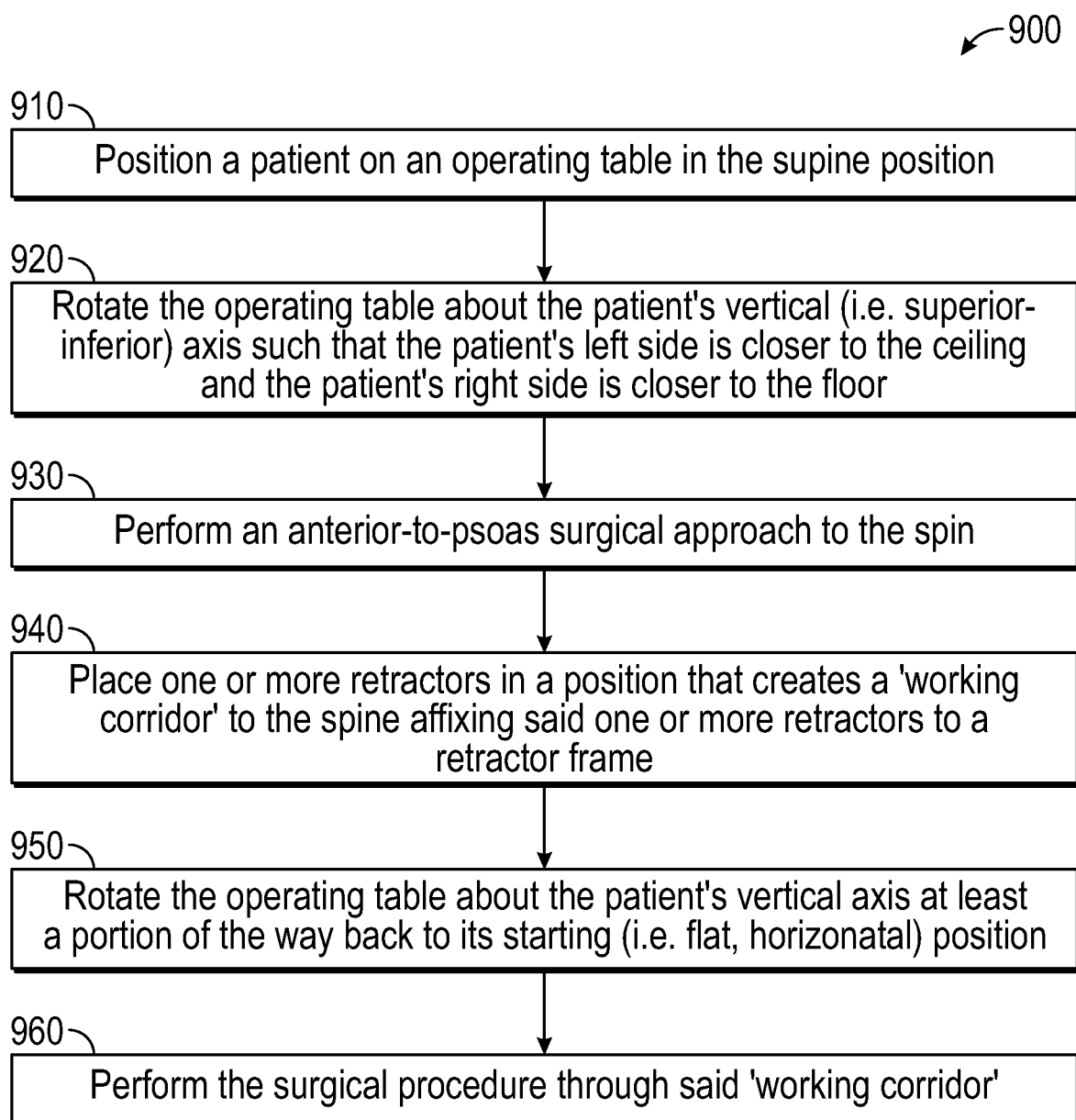
FIG. 9 shows an exemplary method of surgically approaching the spine of a patient for spinal intervertebral implantation.

FIG. 9 provides for at least one embodiment of the method of surgically approaching the spine of a patient for spinal intervertebral implantation. The method 900 shown in FIG. 9 includes step 910 where a patient is positioned on an operating table in the supine position. Next, at step 920, the operating table is rotated about the patient's vertical (i.e. superior-inferior) axis such that the patient's left side is closer to the ceiling and the patient's right side is closer to the floor. At step 930, an anterior-to-psoas (ATP) surgical approach to the spine is performed. At step 940, one or more retractors is/are placed in a position that creates a "working corridor" to the spine affixing the one or more retractors to a retractor frame. A retractor frame generally includes a collection of adjustable components that can, for example, be affixed to the operating table and can provide a means to maintain the position of one or more retractor blades in a rigid manner. Generally, a retractor frame serves the surgeon by providing an independent (i.e. without human intervention) means to maintain the operative corridor by resisting retractor blade movement relative to the patient when forces that may occur during the course of the procedure act on the retractor blades. At step 950, the operating table is rotated about the patient's vertical axis at least a portion of the way back to its starting (i.e. flat, horizontal) position. At step 960, the surgical procedure is performed through the working corridor.

In at least one embodiment, interbody fusion devices are used as a cervical cage implant or thoracic cage implants. The uses of the implant for these purposes may be used across multiple surgical approaches.

In some embodiments, methods may include selecting the size of the interbody fusion device. In at least one embodiment, the size is first determined by measuring the posterior height. Sizing factors include determining such height sufficient to decompress the nerves and/or stabilize the spine. Other sizing considerations include determining the angle of the device necessary to restore proper spinal alignment. In at least one embodiment, spinal alignment is determined by alignment within the sagittal plane. In at least one embodiment, spinal alignment is determined by alignment within the frontal plane. In at least one embodiment, spinal alignment is determined by alignment within both the sagittal plane and the frontal plane.

One exemplary Lordotic Angle Sizing before Posterior Height Sizing Method includes the steps of (1) expose during a discectomy an intervertebral disc space of the spine at the level or levels in which treatment is required, (2) position one or more members against one or more vertebral endplates adjacent to said intervertebral disc space, (3)

determine the angle formed between the member and the device by rotating the one or more members about an axis in the transverse plane and against said one or more vertebral endplates to create the desired degree (i.e. amount) of angulation (e.g. lordosis) with the adjacent vertebrae, (4) insert one or more distraction/measurement device into a posterior region of the intervertebral disc space to determine intervertebral disc space height, (5) assess the fit of said distraction/measurement device between the two adjacent vertebrae until the tightness of the fit desired is achieved, (6) remove the device and one or more members from the intervertebral space, and (7) implant the intevertebral implant size that approximates the selected posterior thickness and lordotic angle.

One exemplary Lordotic Angle Sizing Only Method includes the steps of (1) expose during a discectomy an intervertebral disc space of the spine at the level or levels in which treatment is required, (2) position one or more members against one or more vertebral endplates adjacent to said intervertebral disc space, (3) determine the angle formed between the member and the device by rotating the one or more members about an axis in the transverse plane and against said one or more vertebral endplates to create the desired degree (i.e. amount) of angulation (e.g. lordosis) with the adjacent vertebrae, and (4) implant the intevertebral implant size that approximates the selected posterior thickness and lordotic angle.

One exemplary Posterior Height Sizing Only Method includes the steps of (1) expose during a discectomy an intervertebral disc space of the spine at the level or levels in which treatment is required, (2) insert one or more distraction/measurement device into a posterior region of the intervertebral disc space to determine intervertebral disc space height, (3) assess the fit of said distraction/measurement device between the two adjacent vertebrae until the tightness of the fit desired is achieved, (4) remove the device and one or more members from the intervertebral space, and (5) implant the intevertebral implant size that approximates the selected posterior thickness and lordotic angle.

In at least one embodiment, the method for determining spinal interbody fusion device sizing includes exposing, during a discectomy, an intervertebral disc space of the spine at the level or levels in which treatment is required, completing the discectomy, inserting one or more distraction/measurement devices into a posterior region of the intervertebral disc space to determine intervertebral disc space height and assessing the fit of said distraction/measurement device between the two adjacent vertebrae, determining the thickness of the spacer by inserting one or more progressively thicker distraction/measurement device(s) into the posterior region of the intervertebral disc space until the fit desired is achieved, positioning a member against vertebral endplates adjacent to said intervertebral disc space. In at least one embodiment the member interrelates with the final selected distraction/measurement device at its distal end and can be rotated about an axis in the transverse plane that points to the patients' right and left. In at least one embodiment, the distraction/measurement device, when positioned against the vertebral endplate, has the ability to distract with force to the determined posterior height.

One exemplary method includes determining the lordotic angle formed between the member and the device by rotating the member about an axis in the transverse plane that points to the patients' right and left and against said vertebral endplate to create the desired degree (i.e. amount) of lordosis with the adjacent vertebrae, removing the device and member from the intervertebral space, and implanting the spinal interbody fusion or disc replacement device size that approximates the lordotic angle. While any spinal interbody fusion device known in the art may be used, in certain embodiments, the spinal interbody fusion or disc replacement device(s) disclosed herein is/are used.

One exemplary method includes inserting one or more distraction/measurement devices into a posterior region of the intervertebral disc space to determine intervertebral disc space height and assessing the fit of said distraction/measurement device between the two adjacent vertebrae, removing the device and member from the intervertebral space, and implanting the spinal interbody fusion or disc replacement device size that approximates the posterior thickness. While any spinal interbody fusion device known in the art may be used, in certain embodiments, the spinal interbody fusion or disc replacement device(s) disclosed herein is/are used.

In some embodiments, additional steps may be introduced to allow for better or more accurate measurement. In at least one embodiment, a posterior annulotomy is performed after completing the discectomy. While a typical posterior disc space height is between 2 mm and 10 mm, these may differ depending on patient. Accordingly, a distraction/measurement device used herein can include the ability to distract in increments, e.g., for example, from 4 mm to 10 mm. Additionally, in at least one exemplary embodiment, an exemplary implant system can include ranges of posterior height from 5 mm to 13 mm and anterior heights from 10 mm to 20 mm.

In at least one embodiment, improvements in the measuring process are included which allow for the distraction/measurement device to have progressive posterior heights, e.g., for example, in increments from 4 mm to 10 mm, be distinct from the distraction/measurement device, be connected to the distraction/measurement device, be a part of the distraction/measurement device, or combinations thereof.

Exemplary embodiments of the present disclosure allow for surgical methods to be used in association with one or more spinal interbody fusion or disc replacement device. Such methods may be used with any spinal interbody fusion or disc replacement device, and nothing herein is intended to limit the surgical methods strictly to the use of the spinal interbody fusion devices disclosed.

In at least one embodiment, the Supine/ATP surgical method for approaching the spine of a patient for spinal interbody fusion device implant includes positioning a patient on an operating table in the supine position. For certain patients, and in anticipation of the shift in forces as a result of rotating the operating table, one or more means for securing the patient to the table may be implemented. In at least one embodiment, one or more stabilizing buttress is used along the patient's right side to provide a securing means of the patient to the operating table. In at least one embodiment, two or more hip positioners along the patient's right thigh and just under the axilla are used to serve as a buttress. In at least one embodiment, use of tape stretched across the patient's chest and legs is used to affix the patient to the operating table. One or more means may be used for affixing a patient to the operating table.

Exemplary Supine/ATP surgical method(s) further can include mounting one or more retractor frames to the operating table on the patient's left side, rotating the operating table about the patients' vertical (i.e. superior-inferior) axis such that the patient's left side is closer to the ceiling and the patient's right side is closer to the floor, performing an anterior-to-psoas surgical approach to the spine, placing one or more retractors in a position that creates a 'working corridor' to the spine, affixing the one or more retractors to the one or more retractor frames, rotating the operating table about the patient's vertical axis at least a portion of the way back to its starting (i.e. flat, horizontal) position, and performing the surgical procedure through said 'working corridor'. It should be appreciated that the mounting of the one or more retractor frames can occur just under the axilla and on the right side just above the knee of the patient in certain embodiments.

It should be understood that the above steps are not all inclusive, and additional steps may be implemented as the surgeon sees fit. In at least one embodiment, normal draping and prep for surgery is completed after mounting the one or more retractor frame. In at least one embodiment, the incision made in the surgical procedure on the patient is approximately made at the anterior axillary line on the patient's left side at a level that aligns with the spinal level requiring treatment.

It should be further appreciated that many operating tables exist in the art. While the exemplary method(s) may be performed on any operating table, for optimal results, the operating table should have a capability of being rotated to at least 25°.

Figure 10A:
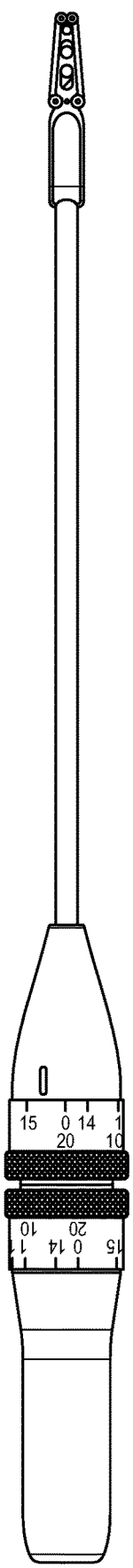
FIGS. 10A through 10E show a posterior referencing lordotic angle sizing instrument.
Figure 10B:
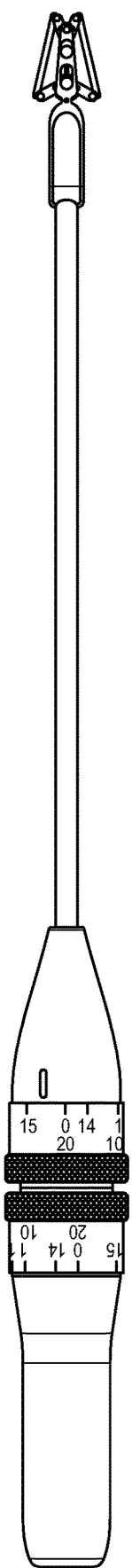
Figure 10C:
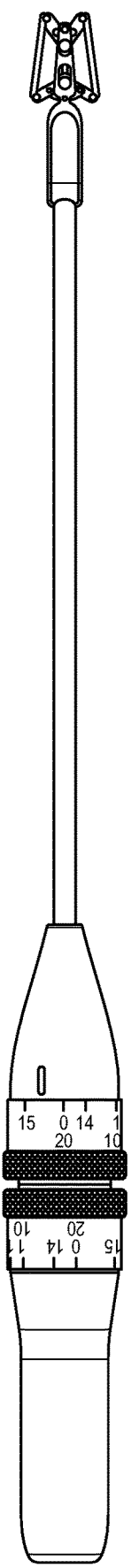
Figure 10D:
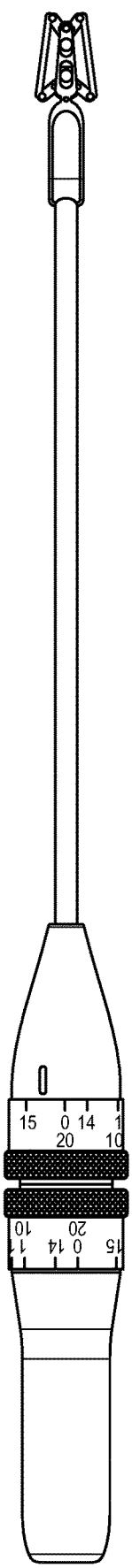
Figure 10E:
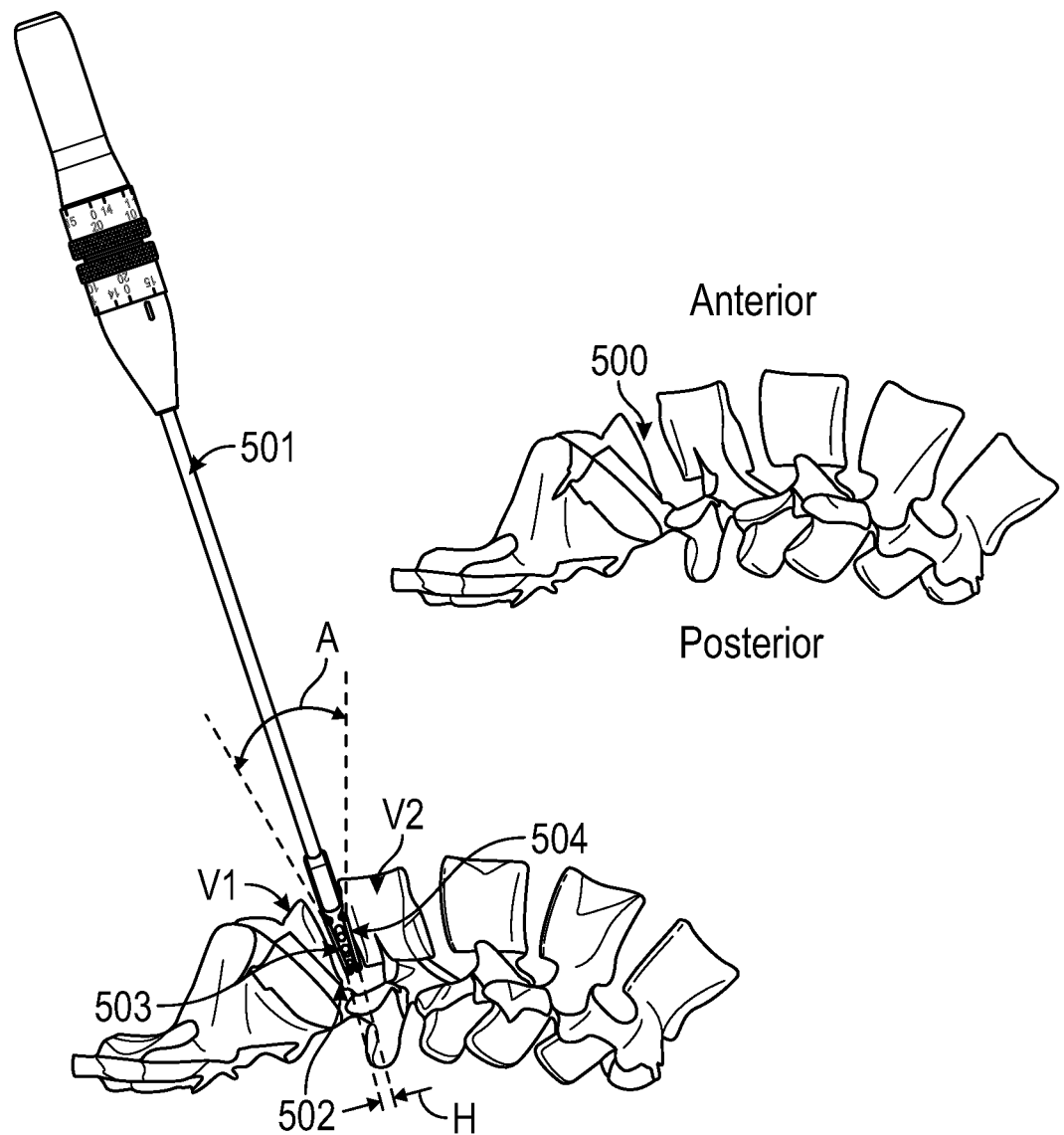

In another aspect, a posterior referencing lordotic angle sizing instrument is provided as shown in FIGS. 10A through 10E. FIG. 10A showing a position with the instrument mostly closed (0% open), FIG. 10B showing a position with the instrument half open (50% open), FIG. 10C showing a position with the instrument in the most open position. FIG. 10D showing a position with the greatest lordotic angle in the most closed position posteriorly and most open position anteriorly. FIGS. 10A through 10D show a surgical instrument that fits within the intervertebral disc space of a human spine with the ability to independently adjust the frontal plane heights of the anterior and posterior regions of the instrument (at least within the range of typical sizes offered in the interbody implant scope) with a means to indicate what these heights are. The instrument also includes a means to indicate the angle formed between the posterior and anterior regions in the sagittal plane and/or a means to indicate the angle formed in the frontal plane. FIG. 10E shows an exemplary use of the instrument of FIGS. 10A through 10D where an intervertebral disc space 500 is exposed during a discectomy at the level or levels in which treatment is required. The use includes one or more distraction/measurement device(s) 501 being inserted into a posterior region 502 of the intervertebral disc space 500 to determine intervertebral disc space height H. After the fit of the distraction/measurement device 501 is assessed between the two adjacent vertebrae V1, V2 until the fit desired is achieved, one or more members 503, 504 is/are positioned against one or more vertebral endplates adjacent to the intervertebral disc space. The angle A formed between the member and the device is determined by rotating the one or more members about an axis in the transverse plane and against the one or more vertebral endplates to create the desired degree (i.e. amount) of angulation (e.g. lordosis) with the adjacent vertebrae. After the device and one or more members is/are removed from the intervertebral space, the intervertebral implant size that approximates the selected posterior height and lordotic angle is implanted.

In one aspect, the present disclosure includes a spinal interbody fusion device that includes a cage with a top side, a bottom side, and at least two other sides. The cage includes at least a first opening, a second opening, a third opening, and a fourth opening, with the first opening and the second opening each being configured for interfacing with fasteners. The first opening is positioned on one side and the second opening is positioned on the other side. The at least third opening and the fourth opening being configured for interfacing with an instrument to allow for spinal fusion during one or more surgical approaches.

In at least one aspect, the surface of the first and second openings couples with the surface of the fasteners. In at least one aspect, the fastener can be a screw or anchor. In at least one aspect, the surface of the first opening couples with the surface of the fastener with threads. In at least one aspect, the instrument can be an inserter. In at least one aspect, the surfaces of the third and fourth openings are configured to couple with the surfaces of the instrument. In at least one aspect, the surface of the instrument has threads. In at least one aspect, the second opening or the third opening is angled. In at least one aspect, the interbody fusion device is a lumbar cage implant. In at least one aspect, the one or more surgical approaches can be anterior, anterior-lateral, oblique, anterior to psoas, or lateral. In at least one aspect, the interbody fusion device is a cervical cage implant. In at least one aspect, the interbody fusion device is a thoracic cage implant.

In at least one aspect, the present disclosure includes a method for selecting a size of an intevertebral implant, with the method including the steps of: exposing an intervertebral disc space, inserting one or more measurement devices into a posterior region of the intervertebral disc space to determine height, assessing fit of the one or more measurement devices, positioning one or more members against one or more vertebrae adjacent to the intervertebral disc space, assessing an approximate angle formed between the one or more members and the one or more measurement devices by rotating the one or more members about an axis in a transverse plane, removing the one or more measurement devices and the one or more members from the intervertebral disc space, and implanting an intevertebral implant for a desired surgical outcome.

In at least one aspect, the one or more members abut vertebral endplates. In at least one aspect, the desired surgical outcome is spinal alignment within a sagittal plane. In at least one aspect, an approximate angle is within a frontal plane. In at least one aspect, the method further comprises performing a posterior annulotomy. In at least one aspect, the height is between 5 mm and 13 mm. In at least one aspect, a portion of the one or more measurement devices can measure the height in increments. In at least one aspect, a progressive posterior height distraction device (1) is either distinct from the one or more measurement devices or can be connected to the one or more measurement devices, (2) can be a part of the progressive posterior height distraction device or the one or more measurement devices, or combinations thereof. In at least one aspect, the one or more members interrelate with a final selected distraction/measurement device at a distal end and can be rotated about an axis in the transverse plane. In at least one aspect, a measurement device, when positioned against the endplate, has an ability to distract with force to the height. In at least one aspect, a measurement device has an ability to distract in increments.

In at least one aspect, the present disclosure includes a surgical instrument that fits within an intervertebral disc space of a spine that provides an independent adjustment of a frontal plane heights at anterior and posterior regions of the instrument with a means to indicate what these heights are. In at least one aspect, the instrument includes a means to indicate an angle formed between posterior and anterior regions in a sagittal plane at least at some variations of frontal plane height positions anteriorly and posteriorly.

In at least one aspect, the present disclosure includes a surgical instrument that fits within an intervertebral disc space of a spine that provides a means to adjust a sagittal and/or frontal plane angle(s) of two endplate-facing surfaces with a means to indicate an angle formed between the two surfaces. In at least one aspect, the instrument includes a means to indicate a height formed at posterior and anterior regions of the instrument at least at some variations of angular positions formed between the two endplate-facing surfaces.

In at least one aspect, the present disclosure includes a method of surgically approaching a spine of a patient for spinal intervertebral implant, with the method including the steps of: positioning a patient on an operating table in a supine position, rotating the operating table about a vertical axis of the patient's vertical (i.e. superior-inferior) axis such that the patient's left side is closer to the ceiling and the patient's right side is closer to the floor, performing an anterior-to-psoas surgical approach to a spine, placing one or more retractors in a position that creates a working corridor to the spine, affixing the one or more retractors to a retractor frame, rotating the operating table about the patient's vertical axis at least a portion of a way back to a starting position (i.e. flat, horizontal), and performing a surgical procedure through the working corridor.

In at least one aspect, the method includes using one or more stabilizing buttress along the right side of the patient. In at least one aspect, the method includes using two or more hip positioners along a right thigh of the patient and just under the axilla to serve as a buttress. In at least one aspect, the method includes using tape stretched across the patient's chest and legs and affix to the operating table. In at least one aspect, the method includes mounting said one or more retractor frame just under the axilla and on the right side just above the knee of the patient. In at least one aspect, the method includes completion normal draping and prep for surgery after mounting said one or more retractor frame. In at least one aspect, an incision is approximately made at the anterior axillary line on the patient's left side at a level that aligns with a spinal level requiring treatment. In at least one aspect, the operating table is rotated to the extent of the table's rotation and wherein the rotation is at least 25°. In at least one aspect, the conventional anatomic pathway is the lateral 'ATP' approach. In at least one aspect, a portion of the surgical procedure includes the final exposure of the spine. In at least one aspect, a portion of the surgical procedure is a conventional spinal discectomy and interbody implantation. In at least one aspect, the intervertebral implant is an interbody fusion device. In at least one aspect, the intervertebral implant is a disc replacement device.

While at least one exemplary embodiment has been presented in the foregoing detailed description, it should be appreciated that a vast number of variations exist. The exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The foregoing description is illustrative of particular embodiments of the disclosure, but is not meant to be a limitation upon the practice thereof. The following claims, including all equivalents thereof, are intended to define the scope of the disclosure.

The invention claimed is:

1. A spinal interbody fusion cage, comprising:
   a plurality of sides, including: a top, a bottom, a back, a front along a width of the cage, and at least two other sides including at least a first side and a second side along a length of the cage;
   two inserter openings and five bone fastener openings;
   wherein a first bone fastener opening of the five bone fastener openings is in the front of the cage and is configured for accepting a first bone fastener in an approximately anterior to posterior direction;
   wherein a second bone fastener opening is in the first side of the cage and is configured for accepting a second bone fastener in an approximately oblique direction;
   wherein the at least five bone fastener openings extend from an exterior of the cage to an interior of the cage;
   wherein a first inserter opening of the two inserter openings is in the front of the cage and a second inserter opening of the two inserter openings is in the first side of the cage;
   wherein the first inserter opening is configured for interfacing with and coupling to a surgical instrument to allow the cage to be inserted in the approximately anterior direction or an approximately lateral direction; and,
   wherein the second inserter opening is configured for interfacing with and coupling to the surgical instrument to allow the cage to be inserted in an approximately oblique direction.

2. The cage of claim 1 wherein the bone fasteners either are a screw or an anchor.

3. The cage of claim 1 wherein the surgical instrument is an inserter.

4. The cage of claim 1 wherein the two inserter openings extend from the exterior of the cage into an interior of the cage.

5. The cage of claim 1 wherein the interbody fusion cage is a lumbar cage implant, a cervical cage implant, or a thoracic cage implant.

6. The cage of claim 1 wherein the cage can be used for one or more surgical approaches, including: anterior, anterior-lateral, oblique, anterior to psoas, or lateral.

7. The cage of claim 1 wherein the interbody fusion cage is a cervical cage implant configured to be used for a plurality of surgical approaches.

8. The cage of claim 1 further comprising a third inserter opening and wherein a third opening is configured to couple with a first instrument to allow a first approach to a spine, and the third opening is configured to couple with the first instrument or another instrument to allow for a second approach to the spine, wherein the first surgical approach is different than the second surgical approach.

9. The cage of claim 1 further comprising a third inserter opening and wherein the third inserter opening is configured to couple with a first instrument to allow a first surgical approach to the spine, and a third opening is configured to couple with the first instrument or another instrument to allow for a second surgical approach and a third surgical approach to the spine, wherein the first surgical approach is different than the second and third surgical approach.

10. The cage of claim 1 further comprising a third inserter opening and wherein the third inserter opening is configured to couple with a first instrument to allow a first surgical approach and second surgical approach to the spine, and the third inserter opening is configured to couple with the first instrument or another instrument to allow for a third surgical approach to the spine, wherein the first surgical approach is different than the second and third surgical approach.

11. The cage of claim 1 further comprising a fourth inserter opening and wherein the third inserter opening is configured to couple with a first instrument to allow an anterior surgical approach to a spine, and the fourth opening is configured to couple with the first instrument or another instrument to allow for an anterior to psoas surgical approach to the spine.

12. The cage of claim 1 further comprising a fourth inserter opening and wherein the third inserter opening is configured to couple with a first instrument to allow anterior and anterior lateral surgical approaches to a spine, and the fourth opening is configured to couple with the first instrument or another instrument to allow for anterior to psoas and oblique surgical approaches to the spine.

13. The cage of claim 1 further comprising a fourth inserter opening and wherein the third inserter opening is configured to couple with a first instrument to allow a first surgical approach to a spine, the fourth inserter opening is configured to couple with the first instrument or another instrument to allow for a second surgical approach to the spine, and a fifth inserter opening is configured to couple with the first instrument or another instrument to allow a third surgical approach to the spine, wherein the first surgical approach is different than the second and third surgical approach.

14. The cage of claim 1 further comprising a fourth inserter opening and wherein the third inserter opening is configured to couple with a first instrument to allow anterior and anterior lateral surgical approaches to a spine, and the fourth inserter opening is configured to couple with the first instrument or another instrument to allow for anterior to psoas and oblique surgical approaches to the spine, and a fifth opening is configured to couple with the first instrument or another instrument to allow for a trans psoas surgical approach to the spine.

15. A surgical method of using an inserter for installation of a cage comprising a plurality of sides, including a top, a bottom, a front along a width of the cage, a back, and at least two other sides including at least a first side and a second side along a length of the cage;
  wherein the cage comprises a first bone fastener opening, a second bone fastener opening, a third bone fastener opening, a first inserter opening, and a second inserter opening;
  wherein the first bone fastener opening is configured for interfacing with a first bone fastener and the second bone fastener opening is configured for interfacing with a second bone fastener;
  wherein the first bone fastener opening and the second bone fastener opening extend through the cage to an interior of the cage;
  wherein the first bone fastener opening is in the front along the width of the cage, the second bone fastener opening is in the first side along the length of the cage;
  wherein the first inserter opening is in the front of the cage and the second inserter opening is in the first side of the cage;
  wherein the cage is capable of interfacing with and coupling to an inserter in the first inserter opening or the second inserter opening and being capable of being affixed to a bone using one or more bone fasteners in the first bone fastener opening or the second bone fastener opening; and,
  wherein the cage is configured for interfacing with the inserter for spinal fusion, the method comprising:
  positioning the cage during surgery with the inserter coupled to:
    the first inserter opening to insert the cage in an approximately anterior to posterior direction or an approximately lateral direction;
    the second inserter opening to insert the cage in an oblique direction; and,
  installing the first bone fastener in the first bone fastener opening of the cage in the approximately anterior direction.

16. The method of claim 15 wherein the cage is a lumbar cage implant, a cervical cage implant, or a thoracic cage implant.

17. The method of claim 15 wherein the cage can be used for one or more surgical approaches, including: anterior, anterior-lateral, oblique, anterior to psoas, or lateral.

18. The method of claim 15 wherein the interbody cage is a cervical cage implant wherein the cage can be used for one or more surgical approaches, including: anterior, anterior-lateral, oblique, lateral to esophagus, lateral to trachea, or lateral.

19. A spinal interbody fusion cage, comprising:
  six sides, including: a top, a bottom, a back, a front along a width of the cage, and at least two other sides including at least a first side along a length of the cage;
  a first opening, a second opening, a third opening, and a fourth opening;
  wherein the first opening is in the front of the cage and is configured for interfacing with and accepting a first bone fastener in an approximately anterior to posterior direction;
  wherein the second opening is in the first side of the cage and is configured for accepting a second bone fastener in an approximately oblique direction;
  wherein the first opening and the second opening extend through the cage to an interior of the cage;
  wherein the first opening and the third opening are in the front of the cage and the second opening and the fourth opening are in the first side of the cage;
  wherein the cage is configured for interfacing with an instrument for spinal fusion; and,
  wherein the third opening is capable of interfacing with and coupling to an inserter to allow the cage to be inserted in the approximately posterior direction and the fourth opening is configured for interfacing with and coupling to the inserter to allow the cage to be inserted in an approximately oblique direction, the cage is capable of being affixed to a bone using one or more bone fasteners in the first opening in the front along the width of the cage and in the second opening on the first side along the length of the cage.

20. The cage of claim 19 wherein the cage is configured to couple with a first instrument to allow at least an anterior surgical approach and with the first instrument or another instrument to allow for an anterior to psoas surgical approach to a spine.

* * * * *